(12) United States Patent
Drewry et al.

(10) Patent No.: US 7,276,523 B2
(45) Date of Patent: Oct. 2, 2007

(54) AMINOPYRIDINE DERIVATIVES AS ESTROGEN RECEPTOR MODULATORS

(75) Inventors: David Harold Drewry, Durham, NC (US); Brad Richard Henke, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 612 days.

(21) Appl. No.: 10/473,087

(22) PCT Filed: Mar. 20, 2002

(86) PCT No.: PCT/US02/08624

§ 371 (c)(1),
(2), (4) Date: Mar. 23, 2004

(87) PCT Pub. No.: WO02/079163

PCT Pub. Date: Oct. 10, 2002

(65) Prior Publication Data

US 2004/0152688 A1    Aug. 5, 2004

Related U.S. Application Data

(60) Provisional application No. 60/280,049, filed on Mar. 30, 2001.

(51) Int. Cl.
*A61K 31/4545* (2006.01)
*C07D 401/04* (2006.01)

(52) U.S. Cl. .................. 514/318; 514/318; 514/340; 546/208; 546/257

(58) Field of Classification Search ............... 546/257, 546/304, 208; 514/340, 352, 318
See application file for complete search history.

(56) References Cited

FOREIGN PATENT DOCUMENTS

WO     99/32447     7/1999
WO     02/22601     3/2002

OTHER PUBLICATIONS

Katritsky, et al "Synthesis of 2-alkylamino- and 2-dialkylamino-4,6-diarylpyridines and 2,4,6-trisubstituted pyrimidines using solid-phase bound chalcones," J. Comb. Chem, 2000, vol. 2, No. 2, pp. 182-185.*
Katritsky et al, "Benzotriazole-assisted preparations of 2-(sunstituted amino) pyridines and pyrid-2-ones," J. Org. Chem, 1997, vol. 62, No. 18, pp. 6210-6214.*
CAPLUS Accession No. 1991:429240, abstract of Shaihla, V et al, "Synthesis and antibacterial activity of some new fluorinated pyrido[2,3-d] pyrimidine derivatives," Ind. J. Pharm. Sciences, 1990, vol. 52, No. 1, pp. 13-15.*
Katritzki, A.R. et al., "Synthese of 2-alkylamino-and 2-dialkylamino-4,6-diarylpyridines and 2,4,6-trisubstituted Pyrimidines Using Solid-Phase Bound Chalcones," *Journal of Combinatorial Chemistry*, vol. 2, No. 2, Feb. 26, 2000, pp. 182-185.
Henke, B.R., et al., "2-Amino-4,6-Diarylpyridines as Novel Ligands for the Estrogen Receptor," *Bioorganic & Medicinal Chemistry Letters*, vol. 11, No. 14, 2001, pp. 1939-1942.
Katritzky. "Benzotriazole-assisted preparations of 2-(substituted amino)pyridines and pyrid-2-ones," *J. Org. Chem.*, vol. 62, No. 18, 1997, pp. 6210-6214.
Chemical Abstracts, vol. 115, No. 3, 1991, Abstract No. 29072d, p. 749.
Zecher; Kroehnke, *Chem. Ber.*, vol. 94, 1961, pp. 698-704.
Chemical Abstracts, vol. 100, No. 25, 1984, Abstract No. 209593y, p. 575.
Sammour, et al., *J. Chem. U.A.R.*, vol. 14, 1971, pp. 581-593.
Sammour, et al., *J. Chem. U.A.R.*, vol. 13, 1970, pp. 421-431.

* cited by examiner

*Primary Examiner*—Kamal A. Saeed
*Assistant Examiner*—Janet L. Coppins
(74) *Attorney, Agent, or Firm*—John L. Lemanowicz; Kathryn L. Coulter

(57) ABSTRACT

Aminopyridine derivatives of the following formula I which exhibit pharmacological activity at estrogen receptors alpha (ERα) and beta (ERβ) are described herein. The described invention also includes compositions and medicaments containing the aminopyridine derivatives as well as processes for the preparation and use of such compounds, compositions and medicaments.

27 Claims, No Drawings

AMINOPYRIDINE DERIVATIVES AS ESTROGEN RECEPTOR MODULATORS

BACKGROUND OF THE INVENTION

This application claims priority from U.S. Ser. No. 60/280,049 filed Mar. 30, 2001.

The present invention relates to aminopyridines, compositions and medicaments containing the same, as well as processes for the preparation and use of such compounds, compositions and medicaments. Such aminopyridines exhibit pharmacological activity at estrogen receptors alpha (ERα) and beta (ERβ).

Estrogens are endocrine regulators in the cellular processes involved in the development and maintenance of the reproductive system. Estrogens have also been shown to have important effects in many non-reproductive tissues such as bone, liver, the cardiovascular system, and the central nervous system. Estrogens exert their effects by binding to an intracellular steroid hormone receptor. After the receptor and bound ligand are translocated to the nucleus of the cell, the complex binds to recognition sites in DNA, which allows for the modulation of certain genes. Certain estrogens have demonstrated the ability to exhibit their biological activity in a "tissue-selective" manner, functioning as estrogen agonists in certain tissues, while acting as estrogen antagonists in other tissues. The term "selective estrogen receptor modulators" (SERMs) has been given to these molecules, examples of which include tamoxifen, raloxifene, lasofoxifene, clomiphene, and nafoxidine. The molecular basis for this tissue selective activity is not completely understood. However, it is thought to involve the ability of the ligand to place the estrogen receptor into different conformational states, which allow for differential capabilities in recruiting coactivator and corepressor proteins as well as other important proteins involved in transcriptional regulation (see McDonnell, D. P., "*The molecular pharmacology of SERMs*", Trends Endocrinol). Metab. 1999, 301-311).

Historically, it was thought that estrogens manifested their biological activity through a single estrogen receptor, now termed estrogen receptor alpha (ERα). However, a second subtype of estrogen receptor, termed estrogen receptor beta (ERβ), has recently been discovered (Kuiper G. G. J. M. et al., WO 9709348; Kuiper, G. G. J. M. et. al., "*Cloning of a novel estrogen receptor expressed in rat prostate and ovary*", Proc. Natl. Acad. Sci. U.S.A. 1996, 5925-5930). ERβ is known to be expressed in humans (Mosselman, S. et. al., "*ERα: identification and characterization of a novel human estrogen receptor*", FEBS Lett 1996, 49-53). The discovery of this second subtype of estrogen receptor significantly increased the biological complexity of estrogen signaling and may be responsible for some, but not all, of the tissue-selective actions of the currently available SERMs.

Osteoporosis is characterized by the net loss of bone mass per unit volume. The consequence of this bone loss is failure of the skeleton to provide adequate structural support for the body, resulting in increased incidence of fracture. One of the most common types of osteoporosis is postmenopausal osteoporosis, which is associated with accelerated bone loss subsequent to cessation of menses and declining levels of endogenous estrogen in women. The inverse relationship between densitometric measures of bone mass and fracture risk, for per- and postmenopausal women in the process of rapid bone loss due to declining levels of estrogen, has been clearly established (Slemenda, C. W. et. al., "*Predictors of bone mass in perimenopausal women, a prospective study of clinical data using photon absorptiometry*", Ann. Intern. Med. 1990, 96-101; Marshall, D. et al., "*Meta-analysis of how well measures of bone mineral density predict occurrence of osteoporotic fractures*", Br. Med. J. 1996, 1254-1259). Elderly women currently have a lifetime risk of fractures of ca. 75%, with a 40% risk of hip fracture for white women over age 50 in the United States. The economic burden from osteoporotic fractures is considerable because of the necessity of hospitalization. In addition, although osteoporosis is generally not thought of as life threatening, the mortality within 4 months of hip fracture is currently 20 to 30%. Current therapies for postmenopausal osteoporosis include estrogen replacement therapy or treatment with other antiresorptive agents such as bisphosphonates or calcitonin. However, patient compliance is low with all these therapies due to undesirable side effects or lack of efficacy.

Cardiovascular disease is the leading cause of death among postmenopausal women. The preponderance of data suggests that estrogen replacement therapy in postmenopausal women reduces the risk of cardiovascular disease, although some studies have reported no beneficial effect on overall mortality (Barrett-Connor, E. et. al., "*The potential of SERMs for reducing the risk of coronary heart disease*", Trends Endocrinol. Metab. 1999, 320-325). The mechanism(s) by which estrogens exert their beneficial effects on the cardiovascular system are not entirely clear, but are potentially linked to their effects on serum cholesterol and lipoproteins, antioxidant properties, vascular smooth muscle proliferation, and inhibition of arterial cholesterol accumulation (Barrett-Connor, E. et. al., "*The potential of SERMs for reducing the risk of coronary heart disease*", Trends Endocrinol. Metab. 1999, 320-325; Cosman, F; Lindsay, R. "*Selective estrogen receptor modulators: clinical spectrum*", Endocrine Rev. 1999, 418-434).

The effects of estrogens on breast tissue, particularly breast cancer, have been well documented. The tissue selective estrogen tamoxifen has conclusively been shown to decrease the risk of recurrent breast cancer, contralateral breast cancer, and mortality as well as increase the disease-free survival in patients with breast cancer at multiple stages of the disease (Cosman, F; Lindsay, R. "*Selective estrogen receptor modulators: clinical spectrum*", Endocrine Rev. 1999, 418-434). However, the mixed agonist-antagonist profile of tamoxifen is not ideal and may have stimulatory effects on uterine cell populations, leading to a potential increase in uterine cancer. An improved therapy for the treatment of these cancers would be an estrogen with no agonist properties on any reproductive tissues.

The present inventors have now discovered a novel group of aminopyridine compounds, which bind to and modulate estrogen receptor alpha and estrogen receptor beta. These compounds also show good tissue-selective estrogenic activity and are therefore of use in the treatment and/or prophylaxis of postmenopausal osteoporosis, estrogen-dependent breast cancer, and cardiovascular disease. These compounds are also indicated to be of use for the treatment and/or prophylaxis of other diseases including dyslipidemia, relief of menopausal vasomotor symptoms, Alzheimer's disease, uterine cancer, prostate cancer, prostate hyperplasia, urinary incontinence, atherosclerosis, uterine fibroid disease, aortic smooth muscle cell proliferation and endometriosis.

BRIEF SUMMARY OF THE INVENTION

In one aspect of the present invention, there is provided a compound of Formula (I):

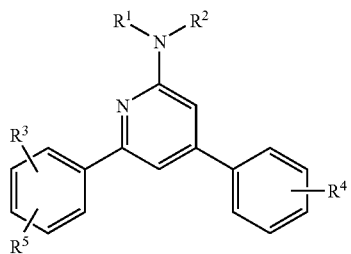

or a salt, solvate, or physiologically functional derivative thereof, wherein $R^1$ and $R^2$ are independently selected from hydrogen, $C_1$-$C_6$ alkyl, $C_1$-$C_6$ haloalkyl, $C_1$-$C_6$ alkoxy, $C_3$-$C_7$ cycloalkyl, aryl, heteroaryl, —(CH$_2$)$_m$R$^6$; or $R^1$ and $R^2$ are both $C_1$-$C_6$ alkylene and are linked together with the nitrogen to which they are attached to form a heterocyclic group;

$R^3$, $R^4$, and $R_5$ are independently selected from hydrogen, hydroxy, ($C_1$-$C_6$)alkyl, halo, or —OR';

m is 0, 1, 2, 3, 4, 5, or 6;

$R^6$ is aryl, heteroaryl, —NR'R", or —OR'; and

R' and R" are independently selected from hydrogen, or $C_1$-$C_6$ alkyl.

In a second aspect of the present invention, there is provided a pharmaceutical composition including a therapeutically effective amount of a compound of formula I, or a salt, solvate, or a physiologically functional derivative thereof and one or more of pharmaceutically acceptable carriers, diluents and excipients.

In a third aspect of the present invention, there is provided a method of treating a disorder in a mammal, said disorder being mediated by inappropriate estrogen receptor activity, including: administering to said mammal a therapeutically effective amount of a compound of formula I or a salt, solvate or a physiologically functional derivative thereof.

In a fourth aspect of the present invention, there is provided a compound of formula I, or a salt, solvate, or a physiologically functional derivative thereof for use in therapy.

In a fifth aspect of the present invention, there is provided the use of a compound of formula I, or a salt, solvate, or a physiologically functional derivative thereof in the preparation of a medicament for use in the treatment of a disorder mediated by inappropriate estrogen receptor activity.

DETAILED DESCRIPTION

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "alkyl" refers to a straight or branched chain hydrocarbon having from one to twelve carbon atoms, optionally substituted with substituents selected from the group consisting of $C_1$-$C_6$ alkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or $C_1$-$C_6$ perfluoroalkyl, multiple degrees of substitution being allowed. Examples of "alkyl" as used herein include, but are not limited to, methyl, ethyl, n-propyl, isopropyl, n-butyl, isobutyl, t-butyl, n-pentyl, isopentyl, and the like.

As used herein, the term "$C_1$-$C_6$ alkyl" refers to an alkyl group as defined above containing at least 1, and at most 6, carbon atoms. Examples of branched or straight-chained "$C_1$-$C_6$ alkyl" groups useful in the present invention include, but are not limited to, methyl, ethyl, n-propyl, isopropyl, isobutyl, n-butyl, t-butyl, and isopentyl.

As used herein, the term "alkylene" refers to a straight or branched chain divalent hydrocarbon radical having from one to ten carbon atoms, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and lower perfluoroalkyl, multiple degrees of substitution being allowed. Examples of "alkylene" as used herein include, but are not limited to, methylene, ethylene, n-propylene, n-butylene, and the like.

As used herein, the term "$C_1$-$C_6$ alkylene" refers to an alkylene group, as defined above, which contains at least 1, and at most 6, carbon atoms. Examples of "$C_1$-$C_6$ alkylene" groups useful in the present invention include, but are not limited to, methylene, ethylene, n-propylene, and the like.

As used herein, the term "halogen" refers to fluorine, chlorine, bromine, or iodine.

As used herein, the term "halo" refers to fluoro (—F), chloro (—Cl), bromo (—Br), or iodo (—I).

As used herein, the term "$C_1$-$C_6$ haloalkyl" refers to an alkyl group as defined above containing at least 1, and at most 6, carbon atoms substituted with at least one halogen, halogen being as defined herein. Examples of branched or straight chained "$C_1$-$C_6$ haloalkyl" groups useful in the present invention include, but are not limited to, methyl, ethyl, propyl, isopropyl, isobutyl, t-butyl, n-butyl, and isopentyl substituted independently with one or more halogens, e.g., fluoro, chloro, bromo and iodo.

As used herein, the term "$C_3$-$C_7$ cycloalkyl" refers to a non-aromatic cyclic hydrocarbon ring having from three to seven carbon atoms. Exemplary "$C_3$-$C_7$ cycloalkyl" groups include, but are not limited to, cyclopropyl, cyclobutyl, cyclopentyl, cyclohexyl and cycloheptyl.

As used herein, the term "aryl" refers to an optionally substituted benzene ring or to an optionally substituted benzene ring system fused to one or more optionally substituted benzene rings to form, for example, anthracene, phenanthrene, or napthalene ring systems. Exemplary optional substituents include $C_1$-$C_6$ alkyl, $C_1$-$C_6$ haloalkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, halogen, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, $C_1$-$C_6$ perfluoroalkyl, heteroaryl, or aryl, multiple degrees of substitution being allowed. Examples of "aryl" groups include, but are not limited to, phenyl, 2-naphthyl, 1-naphthyl, biphenyl, as well as substituted derivatives thereof.

As used herein the term "aralkyl" refers to the group $R_bR_a$—, where $R_a$ is alkyl and $R_b$ is aryl as defined above.

As used herein, the term "heteroaryl" refers to a monocyclic five to seven membered aromatic ring, or to a fused bicyclic aromatic ring system comprising two of such monocyclic five to seven membered aromatic rings. These heteroaryl rings contain one or more nitrogen, sulfur, and/or oxygen heteroatoms, where N-oxides and sulfur oxides and dioxides are permissible heteroatom substitutions and may be optionally substituted with up to three members selected from a group consisting of $C_1$-$C_6$ alkyl, $C_1$-$C_6$ alkoxy, $C_1$-$C_6$ haloalkyl, $C_1$-$C_6$ alkylsulfanyl, $C_1$-$C_6$ alkylsulfenyl, $C_1$-$C_6$ alkylsulfonyl, oxo, hydroxy, halogen, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, $C_1$-$C_6$ perfluoroalkyl, heteroaryl, or aryl, multiple degrees of substitution being allowed. Examples of "heteroaryl" groups used herein include furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, indazole, and substituted versions thereof.

As used herein, the term "heterocyclic" or the term "heterocyclyl" refers to a three to twelve-membered non-aromatic heterocyclic ring being saturated or having one or more degrees of unsaturation containing one or more heteroatomic substitutions selected from S, S(O), S(O)$_2$, O, or N, optionally substituted with substituents selected from the group consisting of $C_1$-$C_6$ alkyl, $C_1$-$C_6$ haloalkyl, aralkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, halogen, mercapto, amino optionally substituted by alkyl, carboxy, carbamoyl optionally substituted by alkyl, aminosulfonyl optionally substituted by alkyl, nitro, cyano, halogen, or $C_1$-$C_6$ perfluoroalkyl, multiple degrees of substitution being allowed. Such a ring may be optionally fused to one or more other "heterocyclic" ring(s) or cycloalkyl ring(s). Examples of "heterocyclic" moieties include, but are not limited to, tetrahydrofuran, pyran, 1,4-dioxane, 1,3-dioxane, piperidine, pyrrolidine, morpholine, tetrahydrothiopyran, tetrahydrothiophene, and substituted versions thereof.

As used herein, the term "alkoxy" refers to the group $R_aO$—, where $R_a$ is alkyl as defined above and the term "$C_1$-$C_6$ alkoxy" refers to an alkoxy group as defined herein wherein the alkyl moiety contains at least 1, and at most 6 carbon atoms.

As used herein the term "aralkoxy" refers to the group $R_bR_aO$—, where $R_a$ is alkyl and $R_b$ is aryl as defined above.

As used herein, the term "alkylsulfanyl" refers to the group $R_aS$—, where $R_a$ is alkyl as defined above and the term "$C_1$-$C_6$ alkylsulfanyl" refers to an alkylsulfanyl group as defined herein wherein the alkyl moiety contains at least 1, and at most 6, carbon atoms.

As used herein, the term "alkylsulfenyl" refers to the group $R_aS(O)$—, where $R_a$ is alkyl as defined above and the term "$C_1$-$C_6$ alkylsulfenyl" refers to an alkylsulfenyl group as defined herein wherein the alkyl moiety contains at least 1, and at most 6, carbon atoms.

As used herein, the term "alkylsulfonyl" refers to the group $R_aS(O)_2$—, where $R_a$ is alkyl as defined above and the term "$C_1$-$C_6$ alkylsulfonyl" refers to an alkylsulfonyl group as defined herein wherein the alkyl moiety contains at least 1, and at most 6, carbon atoms.

As used herein, the term "oxo" refers to the group =O

As used herein, the term "mercapto" refers to the group —SH.

As used herein, the term "carboxy" refers to the group —COOH.

As used herein, the term "cyano" refers to the group —CN.

As used herein the term "cyanoalkyl" refers to the group —$R_a$CN wherein $R_a$ is $C_1$-$C_6$ alkylene as defined above. Exemplary "cyanoalkyl" groups useful in the present invention include, but are not limited to, cyanomethyl, cyanoethyl, and cyanopropyl.

As used herein, the term "aminosulfonyl" refers to the group —S(O)$_2$NH$_2$.

As used herein, the term "carbamoyl" refers to the group —C(O)NH$_2$.

As used herein, the term "sulfanyl" shall refer to the group —S—.

As used herein, the term "sulfenyl" shall refer to the group —S(O)—.

As used herein, the term "sulfonyl" shall refer to the group —S(O)$_2$— or —SO$_2$—.

As used herein, the term "acyl" refers to the group $R_aC(O)$—, where $R_a$ is alkyl, cycloalkyl, or heterocyclyl as defined herein.

As used herein, the term "aroyl" refers to the group $R_aC(O)$—, where $R_a$ is aryl as defined herein.

As used herein, the term "heteroaroyl" refers to the group $R_aC(O)$—, where $R_a$ is heteroaryl as defined herein.

As used herein, the term "alkoxycarbonyl" refers to the group $R_aOC(O)$—, where $R_a$ is alkyl as defined herein.

As used herein, the term "acyloxy" refers to the group $R_aC(O)O$—, where $R_a$ is alkyl, cycloalkyl, or heterocyclyl as defined herein.

As used herein, the term "aroyloxy" refers to the group $R_aC(O)O$—, where $R_a$ is aryl as defined herein.

As used herein, the term "heteroaroyloxy" refers to the group $R_aC(O)O$—, where $R_a$ is heteroaryl as defined herein.

As used herein, the term "optionally" means that the subsequently described event(s) may or may not occur, and includes both event(s), which occur, and events that do not occur.

As used herein, the term "physiologically functional derivative" refers to any pharmaceutically acceptable derivative of a compound of the present invention, for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry And Drug Discovery, 5$^{th}$ Edition, Vol 1: Principles and Practice, which is incorporated herein by reference to the extent that it teaches physiologically functional derivatives.

As used herein, the term "solvate" refers to a complex of variable stoichiometry formed by a solute (in this invention, a compound of formula (I) or a salt or physiologically functional derivative thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include water, ethanol and acetic acid. Most preferably the solvent used is water.

The compounds of formula (I) as well as salts, solvates, and physiologically functional derivatives thereof have the ability to crystallize in more than one form, a characteristic, which is known as polymorphism, and it is understood that such polymorphic forms ("polymorphs") are within the scope of formula (I). Polymorphism generally can occur as a response to changes in temperature or pressure or both and can also result from variations in the crystallization process. Polymorphs can be distinguished by various physical characteristics known in the art, such as x-ray diffraction patterns, solubility, and melting point As used herein, the term "substituted" refers to substitution with the named substituent or substituents, multiple degrees of substitution being allowed unless otherwise stated.

Certain of the compounds described herein contain one or more chiral atoms, or may otherwise be capable of existing as two enantiomers. The compounds of this invention include mixtures of enantiomers as well as purified enantiomers or enantiomerically enriched mixtures. Also included within the scope of the invention are the individual isomers of the compounds represented by formula (I) above as well as any wholly or partially equilibrated mixtures thereof. The present invention also covers the individual isomers of the compounds represented by the formulas above as mixtures with isomers thereof in which one or more chiral centers are inverted.

In one embodiment, $R^1$ is $C_1$-$C_6$ alkyl or —$(CH_2)_m R^6$. In a preferred embodiment $R^1$ is methyl, ethyl, or propyl. In another preferred embodiment, $R^1$ is —$(CH_2)_m R^6$ where m is 2 and $R^6$ is phenyl, —$OCH_2CH_3$, or —$N(CH_3)_2$.

In one embodiment, $R^2$ is $C_1$-$C_6$ alkyl or —$(CH_2)_m R^6$. In a preferred embodiment $R^2$ is n-butyl or isopentyl. In another preferred embodiment, $R^2$ is —$(CH_2)_m R^6$ where m is 1 or 2 and $R^6$ is phenyl, pyridyl, napthyl, or —$OCH_2CH_3$.

In an alternative embodiment, $R^1$ and $R^2$ are both $C_1$-$C_6$ alkylene and are linked together with the nitrogen to which they are attached to form a heterocyclic group. In a preferred embodiment, $R^1$ is —$CH_2CH_2$-(ethylene) and $R^2$ is —$CH_2CH_2CH_2$-(propylene) and $R^1$ and $R^2$ are linked together with the nitrogen to which they are attached to form a piperidine group substituted with aralkyl, preferably benzyl.

In one embodiment, $R^3$ is hydrogen, $C_1$-$C_6$ alkyl or hydroxy. In a preferred embodiment $R^3$ is hydrogen, methyl, or hydroxy. In a more preferred embodiment, $R^3$ is hydroxy.

In one embodiment, $R^4$ is hydrogen or $C_1$-$C_6$ alkyl. In a preferred embodiment, $R^4$ is hydrogen or methyl. In a more preferred embodiment, $R^4$ is hydrogen.

In one embodiment, $R^5$ is hydrogen, $C_1$-$C_6$ alkyl or hydroxy. In a preferred embodiment, $R^5$ is hydrogen, methyl, or hydroxy. In a more preferred embodiment, $R^5$ is hydrogen.

In one embodiment, $R^1$ is $C_1$-$C_6$ alkyl or —$(CH_2)_m R^6$; $R^2$ is $C_1$-$C_6$ alkyl or —$(CH_2)_m R^6$; $R^3$ is hydrogen, $C_1$-$C_6$ alkyl or hydroxy; $R^4$ is hydrogen or $C_1$-$C_6$ alkyl; and $R^5$ is hydrogen, $C_1$-$C_6$ alkyl or hydroxy.

In another embodiment, $R^1$ and $R^2$ are both $C_1$-$C_6$ alkylene and are linked together with the nitrogen to which they are attached to form a heterocyclic group; $R^3$ is hydrogen, $C_1$-$C_6$ alkyl or hydroxy; $R^4$ is hydrogen or $C_1$-$C_6$ alkyl; and $R^5$ is hydrogen, $C_1$-$C_6$ alkyl or hydroxy.

In a preferred embodiment, $R^1$ is —$CH_2CH_2$-(ethylene) and $R^2$ is —$CH_2CH_2CH_2$-(propylene) and $R^1$ and $R^2$ are linked together with the nitrogen to which they are attached to form a piperidine group substituted with aralkyl, preferably benzyl; $R^3$ is hydrogen, $C_1$-$C_6$ alkyl or hydroxy; $R^4$ is hydrogen or $C_1$-$C_6$ alkyl; and $R^5$ is hydrogen, $C_1$-$C_6$ alkyl or hydroxy.

In one embodiment $R^1$ is methyl, ethyl, or propyl; $R^2$ is n-butyl or isopentyl; $R^3$ is hydrogen, $C_1$-$C_6$ alkyl, or hydroxy; $R^4$ is hydrogen or $C_1$-$C_6$ alkyl; and $R^5$ is hydrogen, $C_1$-$C_6$ alkyl or hydroxy.

In one embodiment $R^1$ is methyl, ethyl, or propyl; $R^2$ is —$(CH_2)_m R^6$ where m is 1 or 2 and $R^6$ is phenyl, pyridyl, napthyl, or —$OCH_2CH_3$; $R^3$ is hydrogen, $C_1$-$C_6$ alkyl, or hydroxy; $R^4$ is hydrogen or $C_1$-$C_6$ alkyl; and $R^5$ is hydrogen, $C_1$-$C_6$ alkyl or hydroxy.

In one embodiment, $R^1$ is —$(CH_2)_m R^6$ where m is 2 and $R^6$ is phenyl, —$OCH_2CH_3$, or —$N(CH_3)_2$.; $R^2$ is —$(CH_2)_m R^6$ where m is 1 or 2 and $R^6$ is phenyl, pyridyl, napthyl, or —$OCH_2CH_3$; $R^3$ is hydrogen, $C_1$-$C_6$ alkyl, or hydroxy; $R^4$ is hydrogen or $C_1$-$C_6$ alkyl; and $R^5$ is hydrogen, $C_1$-$C_6$ alkyl or hydroxy.

In one embodiment, $R^1$ is $C_1$-$C_6$ alkyl or —$(CH_2)_m R^6$; $R^2$ is $C_1$-$C_6$ alkyl or —$(CH_2)_m R^6$; $R^3$ is hydroxy; $R^4$ is hydrogen or methyl; and $R^5$ is hydrogen, methyl or hydroxy.

In one embodiment, $R^1$ is $C_1$-$C_6$ alkyl or —$(CH_2)_m R^6$; $R^2$ is $C_1$-$C_6$ alkyl or —$(CH_2)_m R^6$; $R^3$ is hydroxy; $R^4$ is hydrogen; and $R^5$ is hydrogen.

In one embodiment $R^1$ is methyl, ethyl, or propyl; $R^2$ is —$(CH^2)_m R^6$ where m is 1 or 2 and $R^6$ is phenyl, pyridyl, napthyl, or —$OCH_2CH_3$; $R^3$ is hydroxy; $R^4$ is hydrogen or methyl; and $R^5$ is hydrogen, methyl or hydroxy.

In one embodiment, $R^1$ is —$(CH_2)_m R^6$ where m is 2 and $R^6$ is phenyl, —$OCH_2CH_3$, or —$N(CH_3)_2$.; $R^2$ is —$(CH_2)_m R^6$ where m is 1 or 2 and $R^6$ is phenyl, pyridyl, napthyl, or —$OCH_2CH_3$; $R^3$ is hydroxy; $R^4$ is hydrogen or methyl; and $R^5$ is hydrogen, methyl or hydroxy.

Specific examples of compounds of the present invention include the following:

4-{6-[methyl(2-phenylethyl)amino]-4-phenyl-2-pyridinyl}phenol;
4-{6-[methyl(2-phenylethyl)amino]-(4-hydroxy)phenyl-2-pyridinyl}phenol;
3-{6-[methyl(2-phenylethyl)amino]-(4-hydroxy)phenyl-2-pyridinyl}phenol;
3-{6-[methyl(2-phenylethyl)amino]-(3-hydroxy)phenyl-2-pyridinyl}phenol;
3-{6-[methyl(2-phenylethyl)amino]-4-phenyl-2-pyridinyl}phenol;
3-methyl-4-{6-[methyl(2-phenylmethyl)amino]-4-phenyl-2-pyridinyl}phenol;
4-{4-(2-methylphenyl)-6-[methyl(2-phenylethyl)amino]-2-pyridinyl}phenol;
4-{6-[butyl(methyl)amino]-4-phenyl-2-pyridinyl}phenol;
4-{6-[butyl(methyl)amino]-(4-hydroxy)phenyl-2-pyridinyl}phenol;
3-{6-[butyl(methyl)amino]-(4-hydroxy)phenyl-2-pyridinyl}phenol;
3-{6-[butyl(methyl)amino]-(3-hydroxy)phenyl-2-pyridinyl}phenol;
3-{6-[butyl(methyl)amino]-4-phenyl-2-pyridinyl}phenol;
4-{6-[butyl(methyl)amino]-4-phenyl-2-pyridinyl}-3-methylphenol;
4-[6-[butyl(methyl)amino]-4-(2-methylphenyl)-2-pyridinyl]phenol;
4-{6-[benzyl(methyl)amino]-4-phenyl-2-pyridinyl}-3-methylphenol;

4-{6-[benzyl(methyl)amino]-4-phenyl-2-pyridinyl}phenol;
4-{6-[methyl(1-naphthylmethyl)amino]-4-phenyl-2-pyridinyl}phenol;
3-methyl-4-{6-[methyl(1-naphthylmethyl)amino]-4-phenyl-2-pyridinyl}phenol;
2-methyl-4-{6-[methyl(1-naphthylmethyl)amino]-4-phenyl-2-pyridinyl}phenol;
4-{6-[isopentyl(methyl)amino]-4-phenyl-2-pyridinyl}phenol;
4-{6-[isopentyl(methyl)amino]-4-phenyl-2-pyridinyl}-3-methylphenol;
4-(6-{methyl[2-(2-pyridinyl)ethyl]amino}-4-phenyl-2-pyridinyl)phenol;
3-methyl-4-(6-{methyl[2-(2-pyridinyl)ethyl]amino}-4-phenyl-2-pyridinyl)phenol;
2-methyl-4-(6-{methyl[2-(2-pyridinyl)ethyl]amino}-4-phenyl-2-pyridinyl)phenol;
4-{4-phenyl-6-[propyl(2-pyridinylmethyl)amino]-2-pyridinyl}phenol;
3-methyl-4-{4-phenyl-6-[propyl(2-pyridinylmethyl)amino]-2-pyridinyl}phenol;
4-(6-{benzyl[2-(dimethylamino)ethyl]amino}-4-phenyl-2-pyridinyl)-3-methylphenol;
4-{6-[ethyl(4-pyridinylmethyl)amino]-4-phenyl-2-pyridinyl}-3-methylphenol;
4-[6-(4-benzyl-1-piperidinyl)-4-phenyl-2-pyridinyl]-3-methylphenol;
4-[6-(4-benzyl-1-piperidinyl)-4-phenyl-2-pyridinyl]phenol;
4-{6-[benzyl(2-phenylethyl)amino]-4-phenyl-2-pyridinyl}-3-methylphenol; and
4-{6-[bis(2-ethoxyethyl)amino]-4-phenyl-2-pyridinyl}-3-methylphenol;
or a salt, solvate, or physiologically functional derivative thereof.

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts derived from a nitrogen on a substituent in the compound of formula (I). Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, which are not pharmaceutically acceptable, may be useful in the preparation of compounds of this invention and these form a further aspect of the invention.

While it is possible that, for use in therapy, therapeutically effective amounts of a compound of formula (I), as well as salts, solvates and physiologically functional derivatives thereof, may be administered as the raw chemical, it is possible to present the active ingredient as a pharmaceutical composition. Accordingly, the invention further provides pharmaceutical compositions, which include therapeutically effective amounts of compounds of the formula (I) and salts, solvates and physiological functional derivatives thereof, and one or more pharmaceutically acceptable carriers, diluents, or excipients. The compounds of the formula (I) and salts, solvates and physiologically functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I), or salts, solvates and physiological functional derivatives thereof, with one or more pharmaceutically acceptable carriers, diluents or excipients.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the formula (I) depending on the condition being treated, the route of administration and the age, weight and condition of the patient. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agents can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additives such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I), and salts, solvates and physiologically functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula (I) and salts, solvates and physiologically functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. An effective amount of a salt or solvate, or physiologically functional derivative thereof, may be determined as a proportion of the effective amount of the compound of formula (I) per se.

The compounds of formula (I) and salts, solvates and physiological functional derivatives thereof, have activity at estrogen receptors alpha (ERα) and beta (ERβ). Thereby, it is believed, enabling them to modulate diseases and conditions associated with estrogen or the loss of estrogen, including postmenopausal osteoporosis, breast cancer, Alzheimer's disease, uterine cancer, prostate cancer, cardiovascular disease, postmenopausal vasomotor symptoms, cognitive disorders, urinary incontinence, uterine fibroid disease, endometriosis, and prostatic hyperplasia. Accordingly, the present invention is directed to methods of regulating, modulating, or inhibiting estrogen receptors for the prevention and/or treatment of disorders related to unregulated estrogen receptor activity.

The present invention thus also provides compounds of formula (I) and pharmaceutically acceptable salts or solvates thereof, or physiologically functional derivatives thereof, for use in medical therapy, and particularly in the treatment of disorders mediated by inappropriate estrogen receptor activity.

The inappropriate estrogen receptor activity referred to herein is any estrogen receptor activity that deviates from the normal estrogen receptor activity expected in a particular mammalian subject. Inappropriate estrogen receptor activity may take the form of, for instance, an abnormal increase or decrease in activity, or an aberration in the timing and or control of estrogen receptor activity.

A further aspect of the invention provides a method of treatment of a mammal suffering from a disorder mediated by inappropriate estrogen receptor activity, which includes administering to said subject an effective amount of a compound of formula (I) or a pharmaceutically acceptable salt, solvate, or a physiologically functional derivative thereof.

A further aspect of the present invention provides the use of a compound of formula (I), or a pharmaceutically acceptable salt or solvate thereof, or a physiologically functional derivative thereof, in the preparation of a medicament for the treatment of a disorder characterized by inappropriate estrogen receptor activity.

The mammal requiring treatment with a compound of the present invention is typically a human being.

The compounds of this invention may be made by a variety of methods, including standard chemistry. Any previously defined variable will continue to have the previously defined meaning unless otherwise indicated. Illustrative synthetic methods are set out below for specific compounds of the invention in the working examples following.

Compounds of general formula (I) may be prepared by methods known in the art of organic synthesis as set forth in part by the following working example synthesis. In all of the working examples described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) *Protecting Groups in Organic Synthesis*, John Wiley Et Sons). These groups are removed at a convenient stage of the compound synthesis using methods that are readily apparent to those skilled in the art. The selection of processes as well as the reaction conditions and order of their execution shall be consistent with the preparation of compounds of Formula I. Those skilled in the art will recognize if a stereocenter exists in compounds of Formula I. Accordingly, the present invention includes both possible stereoisomers and includes not only racemic compounds but the individual enantiomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994).

Certain embodiments of the present invention will now be illustrated by way of working examples. The physical data given for the compounds exemplified is consistent with the assigned structure of those compounds.

EXAMPLES

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

| | |
|---|---|
| g (grams); | mg (milligrams); |
| L (liters); | mL (milliliters); |
| μL (microliters); | psi (pounds per square inch); |
| M (molar); | mM (millimolar); |
| i.v. (intravenous); | Hz (Hertz); |
| MHz (megahertz); | mol (moles); |
| mmol (millimoles); | RT (room temperature); |
| min (minutes); | h (hours); |
| mp (melting point); | TLC (thin layer chromatography); |
| $T_r$ (retention time); | RP (reverse phase); |
| MeOH (methanol); | i-PrOH (isopropanol); |
| TEA (triethylamine); | TFA (trifluoroacetic acid); |
| TFAA (trifluoroacetic anhydride); | THF (tetrahydrofuran); |
| DMSO (dimethylsulfoxide); | EtOAc (ethyl acetate); |
| DME (1,2-dimethoxyethane); | DCM (dichloromethane); |
| DCE (dichloroethane); | DMF (N,N-dimethylformamide); |
| DMPU (N,N'-dimethylpropyleneurea); | (CDI (1,1-carbonyldiimidazole); |
| IBCF (isobutyl chloroformate); | HOAc (acetic acid); |
| HOSu (N-hydroxysuccinimide); | HOBT (1-hydroxybenzotriazole); |
| mCPBA (meta-chloroperbenzoic acid; | EDC (ethylcarbodiimide hydrochloride); |
| BOC (tert-butyloxycarbonyl); | FMOC (9-fluorenylmethoxycarbonyl); |
| DCC (dicyclohexylcarbodiimide); | CBZ (benzyloxycarbonyl); |
| Ac (acetyl); | atm (atmosphere); |
| HPLC (high pressure liquid chromatography); | |
| BOP (bis(2-oxo-3-oxazolidinyl)phosphinic chloride); | |
| TBAF (tetra-n-butylammonium fluoride); | |

All references to ether are to diethyl ether; brine refers to a saturated aqueous solution of NaCl. Unless otherwise indicated, all temperatures are expressed in ° C. (degrees Centigrade). All reactions are conducted under an inert atmosphere at room temperature unless otherwise noted.

$^1$H NMR spectra were recorded on a Varian VXR-300, a Varian Unity-300, a Varian Unity-400 instrument, or a General Electric QE-300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet), br (broad).

Low-resolution mass spectra (MS) were recorded on a JOEL JMS-AX505HA, JOEL SX-102, or a SCIEX-APIiii spectrometer; high resolution MS were obtained using a JOEL SX-102A spectrometer. All mass spectra were taken under electrospray ionization (ESI), chemical ionization (CI), electron impact (EI) or by fast atom bombardment (FAB) methods. Infrared (IR) spectra were obtained on a Nicolet 510 FT-IR spectrometer using a 1-mm NaCl cell. All reactions were monitored by thin-layer chromatography on 0.25 mm E. Merck silica gel plates (60F-254), visualized with UV light, 5% ethanolic phosphomolybdic acid or p-anisaldehyde solution. Flash column chromatography was performed on silica gel (230-400 mesh, Merck). Optical rotations were obtained using a Perkin Elmer Model 241 Polarimeter. Melting points were determined using a Mel-Temp II apparatus and are uncorrected.

Preparation of Intermediates

Intermediate 1:

1-[3-(tetrahydro-2H-pyran-2-yloxy)phenyl]ethanone

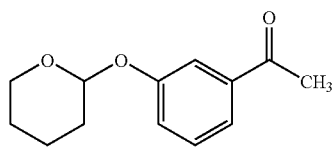

Intermediate 1 was prepared by adaptation of a literature procedure (Chavez et. al., *Synth. Commun.* 1992, 159). A stirred solution of 5.0 g (40.0 mmol) of m-hydroxyacetophenone in 80 mL of DCM at RT was treated with 100 mg of 3% $H_2SO_4$ on silica gel, followed by dropwise addition of 6.7 g (80.0 mmol, 2.0 equiv.) of freshly distilled 3,4-dihydro-2H-pyran. The resulting solution was stirred 15 min at RT, then filtered through a pad of Celite to remove the 3% $H_2SO_4$ on silica gel catalyst. $Et_3N$ (3-4 drops) was added to the filtrate and the solvent was removed in vacuo. Purification of the residue by silica gel flash column chromatography eluting with hexanes/EtOAc 10:1 afforded 8.76 g (99%) of the title compound as a pale yellow oil. $^1$H NMR (CDCl$_3$, 400 MHz) δ 7.77 (s, 1H), 7.71 (d, 1H, J=7.7), 7.50 (dd, 1H, J=8.1), 7.39 (dd, 1H, J=2.5, 8.1), 5.62 (dd, 1H, J=3.3), 4.03 (m, 1H), 3.76 (m, 1H), 2.72 (s, 3H), 2.18-1.83 (m, 6H); TLC (hexanes/EtOAc 2:1) $R_f$=0.50.

Intermediate 2:

1-[4-(tetrahydro-2H-pyran-2-yloxy)phenyl]ethanone

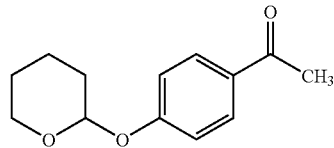

Intermediate 2 was prepared from p-hydroxyacetophenone by an identical procedure as described in the preparation of Intermediate 1 to afford 7.82 g (96%) of the title compound as a clear oil. $^1$H NMR (CDCl$_3$, 400 MHz) δ 7.85 (dd, 2H, J=2.5, 11.4), 7.02 (dd, 2H, J=2.5, 11.4), 5.44 (dd, 1H, J=3.1), 3.77 (m, 1H), 3.55 (m, 1H), 2.49 (s, 3H), 1.94-1.51 (m, 6H); TLC (hexanes/EtOAc 5:1) $R_f$=0.15.

Intermediate 3:

1-[2-methyl-4-(tetrahydro-2H-pyran-2-yloxy)phenyl]ethanone

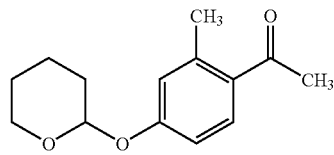

Intermediate 3 was prepared from 2-methyl-4-hydroxyacetophenone by an identical procedure as described in the preparation of Intermediate 1 to afford 7.71 g (100%) of the title compound as a clear oil. $^1$H NMR (CDCl$_3$, 400 MHz) δ 7.82 (d, 1H, J=6.8), 6.91 (m, 2H), 5.42 (dd, 1H, J=3.1), 3.77 (m, 1H), 3.57 (m, 1H), 2.49 (s, 3H), 2.46 (s, 3H), 1.94-1.51 (m, 6H); TLC (hexanes/EtOAc 5:1) $R_f$=0.20.

Intermediate 4:

1-[3-methyl-4-(tetrahydro-2H-pyran-2-yloxy)phenyl]ethanone

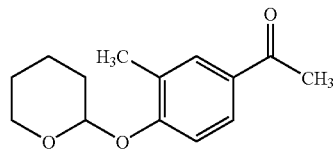

Intermediate 4 was prepared from 3-methyl-4-hydroxyacteophenone by an identical procedure as described in the preparation of Intermediate 1 to afford 7.8 g (100%) of the title compound as a clear oil. $^1$H NMR (CDCl$_3$, 400 MHz) δ 7.80 (m, 2H), 7.03 (d, 1H, J=6.8), 5.53 (dd, 1H, J=3.1), 3.82 (m, 1H), 3.60 (m, 1H), 2.55 (s, 3H), 2.32 (s, 3H), 1.94-1.51 (m, 6H); TLC (hexanes/EtOAc 2:1) $R_f$=0.55.

Intermediate 5:

3-(tetrahydro-2H-pyran-2-yloxy)benzaldehyde

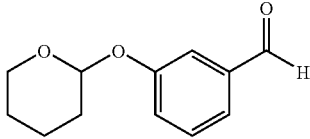

Intermediate 5 was prepared from 3-hydroxybenzaldehyde by an identical procedure as described in the preparation of Intermediate 1 to afford 8.2 g (98%) of the title compound as a clear oil. $^1$H NMR (CDCl$_3$, 400 MHz) δ 10.11 (s, 1H), 7.69 (d, 1 H, J=2.1), 7.63 (dd, 1H, J=6.3, 6.3), 7.58 (dd, 1H, J=7.7, 7.7), 7.44 (m, 1H), 5.63 (dd, 1H, J=3.2), 4.02 (m, 1H), 3.77 (m, 1H), 2.18-1.77 (m, 6H); TLC (hexanes/EtOAc 5:1) R$_f$=0.30.

Intermediate 6:

3-(tetrahydro-2H-pyran-2-yloxy)benzaldehyde

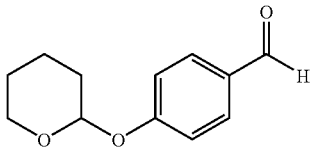

Intermediate 6 was prepared from 4-hydroxybenzaldehyde by an identical procedure as described in the preparation of Intermediate 1 to afford 6.2 g (74%) of the title compound as a clear oil. $^1$H NMR (CDCl$_3$, 400 MHz) δ 9.82 (s, 1H), 7.81 (d, 2H, J=11.1), 7.03 (d, 2H, J=11.1), 5.58 (dd, 1H, J=3.2), 3.84 (m, 1H), 3.66 (m, 1H), 2.08-1.62 (m, 6H); TLC (hexanes/EtOAc 5:1) R$_f$=0.30.

Intermediate 7:

(2E)-1,3-bis[3-(tetrahydro-2H-pyran-2-yloxy)phenyl]-2-propen-1-one

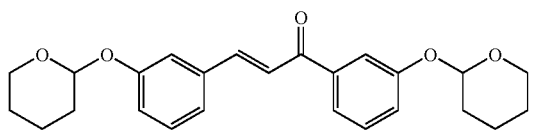

A stirred solution of 1.1 g (5.0 mmol) of Intermediate 1 and 1.0 g (5.0 mmol) of Intermediate 5 in 5 mL of absolute ethanol was treated with 50 mg (1.25 mmol) of finely ground solid NaOH. The resulting yellow solution was stirred overnight at RT. The solvent was removed in vacuo. Purification of the residue by silica gel chromatography (Elution Solutions Prep LC) and eluting with hexanes/EtOAc 6:1 afforded 1.18 g (59%) of the title compound as a pale yellow oil. $^1$H NMR (CDCl$_3$, 400 MHz) δ 7.75 (d, 1H, J=15.7), 7.66 (m, 2H), 7.50-7.25 (m, 6H), 7.12 (d, 1H, J=15.7), 5.49 (m, 1H), 5.45 (m, 1H), 3.89 (m, 2H), 3.63 (m, 2H), 2.04-1.62 (m, 12H); low resolution MS (ES$^+$) m/e 410 (MH$^+$+1), 409 (MH$^+$), 241 (M$^+$−2 THP groups).

Intermediate 8:

(2E)-1,3-bis[4-(tetrahydro-2H-pyran-2-yloxy)phenyl]-2-propen-1-one

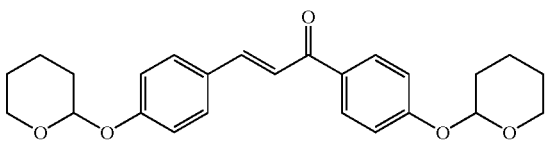

Intermediate 8 was prepared from Intermediate 2 and Intermediate 6 by an identical procedure as described in the preparation of Intermediate 7 to afford 911 mg (46%) of the title compound as a white solid. $^1$H NMR (CDCl$_3$, 400 MHz) δ 8.02 (d, 2H, J=8.9), 7.77 (d, 1H, J=15.8), 7.58 (d, 2H, J=8.9), 7.42 (d, 1H, J=15.8), 7.12 (m, 4 H), 5.53 (dd, 1H, J=3.1, 3.1), 5.48 (dd, 1H, J=3.2, 3.2), 3.89 (m, 2H), 3.62 (m, 2H), 2.02-1.82 (m, 12H); low resolution MS (ES$^+$) m/e 410 (MH$^+$+1), 409 (MH$^+$), 241 (M$^+$−2 THP groups).

Intermediate 9:

(2E)-3-phenyl-1-[4-(tetrahydro-2H-pyran-2-yloxy)phenyl]-2-propen-1-one

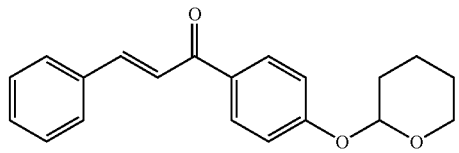

Intermediate 9 was prepared from Intermediate 2 and benzaldehyde by an identical procedure as described in the preparation of Intermediate 7 to afford 785 mg (52%) of the title compound as a light yellow solid. $^1$H NMR (CDCl$_3$, 400 MHz) δ 8.02 (d, 2H, J=8.9), 7.79 (d, 1H, J=15.4), 7.61 (m, 2H), 7.52 (d, 1H, J=15.8), 7.41 (m, 3H), 7.14 (d, 2H, J=8.9), 5.53 (dd, 1H, J=3.1, 3.1), 3.89 (m, 1H), 3.62 (m, 1H), 2.02-1.82 (m, 6H); low resolution MS (ES$^+$) m/e 309 (MH$^+$), 225 (M$^+$−THP group).

Intermediate 10:

(2E)-3-[3-(tetrahydro-2H-pyran-2-yloxy)phenyl]-1-[4-(tetrahydro-2H-pyran-2-yloxy)phenyl]-2-propen-1-one

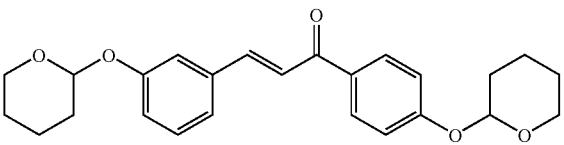

Intermediate 10 was prepared from Intermediate 2 and Intermediate 5 by an identical procedure as described in the preparation of Intermediate 7 to afford 785 mg (52%) of the title compound as a light yellow solid. $^1$H NMR (CDCl$_3$, 400 MHz) δ 8.02 (d, 2H, J=8.9), 7.76 (d, 1H, J=15.5), 7.52 (d, 1H, J=15.5), 7.29 (m, 3H), 7.14 (m, 3 H), 5.54 (dd, 1H, J=3.1, 3.1), 5.47 (dd, 1H, J=3.1, 3.1), 3.89 (m, 2H), 3.62 (m, 2H), 2.05-1.82 (m, 12H); low resolution MS (ES+) m/e 410 (MH++1), 409 (MH+), 241 (M+−2 THP groups).

Intermediate 11:

(2E)-3-phenyl-1-[3-(tetrahydro-2H-pyran-2-yloxy)phenyl]-2-propen-1-one

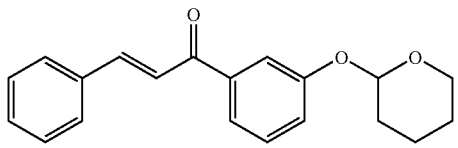

Intermediate 11 was prepared from Intermediate 1 and benzaldehyde by an identical procedure as described in the preparation of Intermediate 7 to afford 785 mg (57%) of the title compound as a light yellow oil. $^1$H NMR (CDCl$_3$, 400 MHz) δ 7.80 (d, 1H, J=15.7), 7.65 (m, 4H), 7.48-7.27 (m, 7H, J=15.8), 5.51 (m, 1H), 3.89 (m, 1H), 3.62 (m, 1H), 2.02-1.65 (m, 6H); low resolution MS (ES+) m/e 309 (MH+), 225 (M+−THP group).

Intermediate 12:

(2E)-1-[2-methyl-4-(tetrahydro-2H-pyran-2-yloxy)phenyl]-3-phenyl-2-propen-1-one

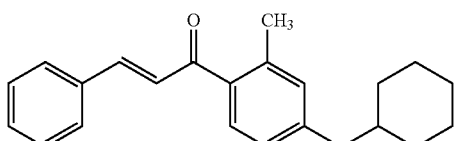

Intermediate 12 was prepared from Intermediate 3 and benzaldehyde by an identical procedure as described in the preparation of Intermediate 7 to afford 1.52 g (95%) of the title compound as a light yellow oil. $^1$H NMR (CDCl$_3$, 400 MHz) δ 7.55 (m, 4H), 7.39 (m, 3H), 7.21 (d, 1H, J=15.9), 6.95 (m, 2H), 5.51 (dd, 1H, J=3.1, 3.1), 3.87 (m, 1H), 3.62 (m, 1H), 2.49 (s, 3H), 2.02-1.65 (m, 6H); low resolution MS (ES+) m/e 323 (MH+), 239 (M+− THP group).

Intermediate 13:

(2E)-3-(2-methylphenyl)-1-[4-(tetrahydro-2H-pyran-2-yloxy)phenyl]-2-propen-1-one

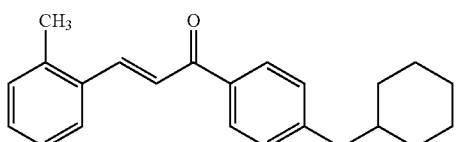

Intermediate 13 was prepared from Intermediate 2 and 2-methylbenzaldehyde by an identical procedure as described in the preparation of Intermediate 7 to afford 1.58 g (9801%) of the title compound as a light yellow oil. $^1$H NMR (CDCl$_3$, 400 MHz) δ 8.04 (m, 3H), 7.69 (d, 1H, J=7.6), 7.46 (d, 1H, J=15.5), 7.29 (m, 3H), 7.13 (d, 2H, J=8.9), 5.54 (dd, 1H, J=3.1, 3.1), 3.84 (m, 1H), 3.62 (m, 1H), 2.47 (s, 3H), 2.02-1.65 (m, 6H); low resolution MS (ES+) m/e 323 (MH+), 239 (M+− THP group).

Intermediate 14:

(2E)-1-[3-methyl-4-(tetrahydro-2H-pyran-2-yloxy)phenyl]-3-phenyl-2-propen-1-one

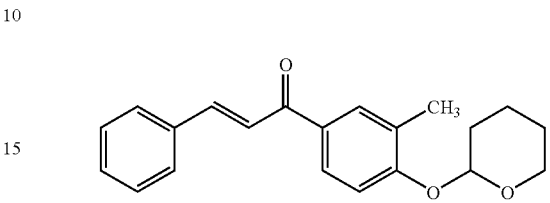

Intermediate 14 was prepared from Intermediate 4 and benzaldehyde by an identical procedure as described in the preparation of Intermediate 7 to afford 1.52 g (95%) of the title compound as a light yellow oil. $^1$H NMR (CDCl$_3$, 400 MHz) δ 7.75 (m, 4H), 7.63 (m, 2H), 7.57 (d, 1H, J=15.9), 7.40 (m, 3H), 5.54 (dd, 1H, J=3.1, 3.1), 3.84 (m, 1H), 3.61 (m, 1H), 2.34 (s, 3H), 2.02-1.65 (m, 6H); low resolution MS (ES+) m/e 323 (MH+), 239 (M+− THP group).

Example 1

4-{6-[methyl(2-phenylethyl)amino]-4-phenyl-2-pyridinyl}phenol

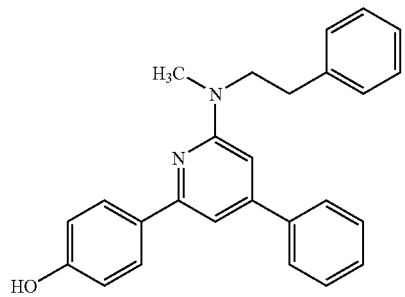

A 1-dram vial containing a solution consisting of 0.05 mmol (15 mg) of Intermediate 9, 0.05 mmol (10 mg) of 1H-1,2,3-benzotriazol-1-ylacetonitrile (Katritzky, A. R. et al., J. Org. Chem. 1997, 62, 6210) and 1.0 mmol (20 equiv, 135 mg) of N-methyl-N-phenethylamine in 1 mL absolute ethanol was placed in a J-Chem heating block set upon an orbital shaker and was shaken at 75° C. for 72 hr. The reaction mixture was allowed to cool to RT, then 1 mL of 80% acetic acid solution was added and the vial shaken at 55° C. for 18 hr. The reaction was allowed to cool to RT and the solvents removed in vacuo. The resulting crude material was purified using silica gel chromatography (5 g silica gel in an Alltech SPE tube using a gradient elution system consisting of hexanes/EtOAc 10:1, 2:1, 1:1, 1:5 and then CHCl$_3$/MeOH 20:1, 9:1 to afford 7 mg of the title compound as a yellow oil. Low resolution MS (ES+) m/e 381 (MH+); RP-HPLC (Dynamax C-18 25 cm×4.1 mm; 10-100% CH$_3$CN in H$_2$O with 0.1% TFA buffer; 30 minutes; 1 mL/min) t$_r$=19.68 min.

Example 2

4-{6-[methyl(2-phenylethyl)amino]-(4-hydroxy)phenyl-2-pyridinyl}phenol

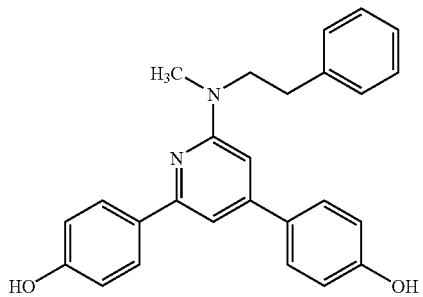

Example 2 was prepared from Intermediate 8, 1H-1,2,3-benzotriazol-1-ylacetonitrile, and N-methyl-N-phenethylamine by an identical procedure as described in Example 1 to afford 5 mg of a yellow oil. Low resolution MS (ES$^+$) m/e 397 (MH$^+$); RP-HPLC (Dynamax C-18 25 cm×4.1 mm; 10-100% CH$_3$CN in H$_2$O with 0.1% TFA buffer; 30 minutes; 1 mL/min) t$_r$=18.41 min.

Example 3

3-{6-[methyl(2-phenylethyl)amino]-(4-hydroxy)phenyl-2-pyridinyl}phenol

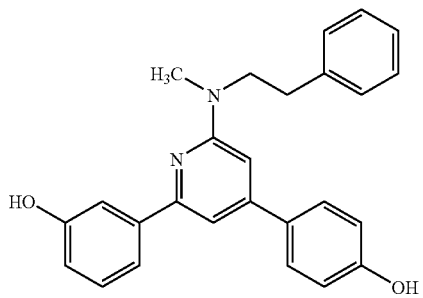

Example 3 was prepared from Intermediate 10, 1H-1,2,3-benzotriazol-1-ylacetonitrile, and N-methyl-N-phenethylamine by an identical procedure as described in Example 1 to afford 3 mg of a yellow oil. Low resolution MS (ES$^+$) m/e 397 (MH$^+$); RP-HPLC (Dynamax C-18 25 cm×4.1 mm; 10-100% CH$_3$CN in H$_2$O with 0.1% TFA buffer; 30 minutes; 1 mL/min) t$_r$=18.62 min.

Example 4

3-{6-[methyl(2-phenylethyl)amino]-(3-hydroxy)phenyl-2-pyridinyl}phenol

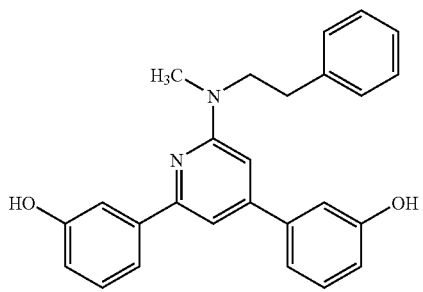

Example 4 was prepared from Intermediate 7, 1H-1,2,3-benzotriazol-1-ylacetonitrile, and N-methyl-N-phenethylamine by an identical procedure as described in Example 1 to afford 8 mg of a yellow oil. Low resolution MS (ES$^+$) m/e 397 (MH$^+$); RP-HPLC (Dynamax C-18 25 cm×4.1 mm; 10-100% CH$_3$CN in H$_2$O with 0.1% TFA buffer; 30 minutes; 1 mL/min) t$_r$=17.95 min.

Example 5

3-{6-[methyl(2-phenylethyl)amino]-4-phenyl-2-pyridinyl}phenol

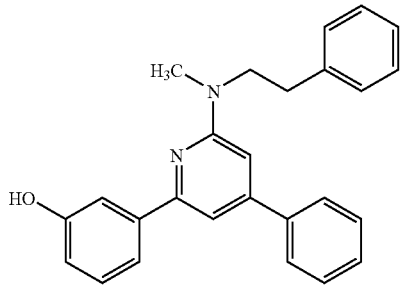

Example 5 was prepared from Intermediate 11, 1H-1,2,3-benzotriazol-1-ylacetonitrile, and N-methyl-N-phenethylamine by an identical procedure as described in Example 1 to afford 6 mg of a yellow oil. Low resolution MS (ES$^+$) m/e 381 (MH$^+$); RP-HPLC (Dynamax C-18 25 cm×4.1 mm; 10-100% CH$_3$CN in H$_2$O with 0.1% TFA buffer; 30 minutes; 1 mL/min) t$_r$=18.91 min.

Example 6

3-methyl-4-{6-[methyl(2-phenylethyl)amino]-4-phenyl-2-pyridinyl}phenol

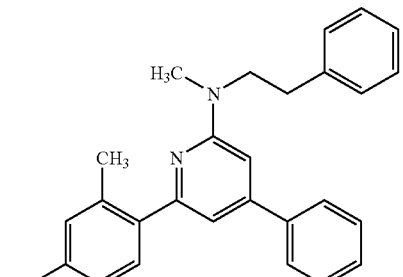

Example 6 was prepared from Intermediate 12, 1H-1,2,3-benzotriazol-1-ylacetonitrile, and N-methyl-N-phenethylamine by an identical procedure as described in Example 1 to afford 9 mg of a yellow oil. Low resolution MS (ES$^+$) m/e 395 (MH$^+$); RP-HPLC (Dynamax C-18 25 cm×4.1 mm; 10-100% CH$_3$CN in H$_2$O with 0.1% TFA buffer; 30 minutes; 1 mL/min) t$_r$=19.43 min.

Example 7

4-{4-(2-methylphenyl)-6-[methyl(2-phenylethyl)amino]-2-pyridinyl}phenol

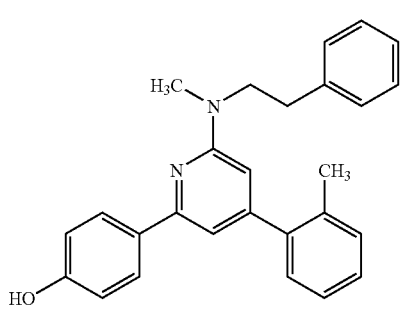

Example 7 was prepared from Intermediate 13, 1H-1,2,3-benzotriazol-1-ylacetonitrile, and N-methyl-N-phenethylamine by an identical procedure as described in Example 1 to afford 9 mg of a yellow oil. Low resolution MS (ES⁺) m/e 395 (MH⁺); RP-HPLC (Dynamax C-18 25 cm×4.1 mm; 10-100% CH₃CN in H₂O with 0.1% TFA buffer; 30 minutes; 1 mL/min) $t_r$=19.22 min.

Example 8

4-{6-[butyl(methyl)amino]-4-phenyl-2-pyridinyl}phenol

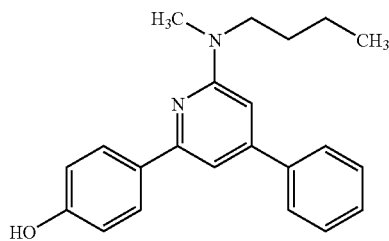

Example 8 was prepared from Intermediate 9, 1H-1,2,3-benzotriazol-1-ylacetonitrile, and N-methyl-N-propylamine by an identical procedure as described in Example 1 to afford 5 mg of a tan oil. Low resolution MS (ES⁺) m/e 333 (MH⁺); RP-HPLC (Dynamax C-18 25 cm×4.1 mm; 10-100% CH₃CN in H₂O with 0.1% TFA buffer; 30 minutes; 1 mL/min) $t_r$=16.73 min.

Example 9

4-{6-[butyl(methyl)amino]-(4-hydroxy)phenyl-2-pyridinyl}phenol

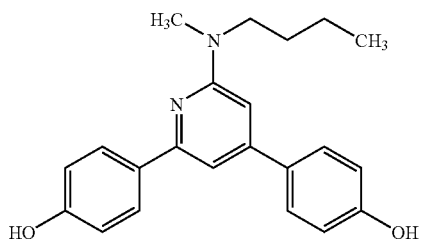

Example 9 was prepared from Intermediate 8, 1H-1,2,3-benzotriazol-1-ylacetonitrile, and N-methyl-N-propylamine by an identical procedure as described in Example 1 to afford 11 mg of a brown oil. Low resolution MS (ES⁺) m/e 349 (MH⁺); RP-HPLC (Dynamax C-18 25 cm×4.1 mm; 10-100% CH₃CN in H₂O with 0.1% TFA buffer; 30 minutes; 1 mL/min) $t_r$=15.11 min.

Example 10

3-{6-[butyl(methyl)amino]-(4-hydroxy)phenyl-2-pyridinyl}phenol

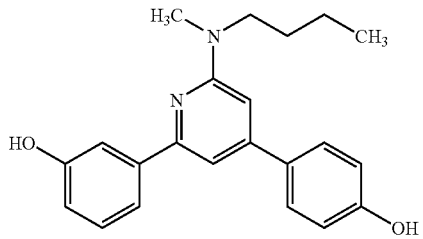

Example 10 was prepared from Intermediate 10, 1H-1,2,3-benzotriazol-1-ylacetonitrile, and N-methyl-N-propylamine by an identical procedure as described in Example 1 to afford 12 mg of a yellow oil. Low resolution MS (ES⁺) m/e 349 (MH⁺); RP-HPLC (Dynamax C-18 25 cm×4.1 mm; 10-100% CH₃CN in H₂O with 0.1% TFA buffer; 30 minutes; 1 mL/min) $t_r$=15.34 min.

Example 11

3-{6-[butyl(methyl)amino]-(3-hydroxy)phenyl-2-pyridinyl}phenol

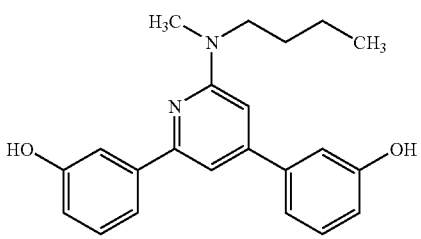

Example 11 was prepared from Intermediate 7, 1H-1,2,3-benzotriazol-1-ylacetonitrile, and N-methyl-N-propylamine by an identical procedure as described in Example 1 to afford 4 mg of a yellow oil. Low resolution MS (ES⁺) m/e 349 (MH⁺); RP-HPLC (Dynamax C-18 25 cm×4.1 mm; 10-100% CH₃CN in H₂O with 0.1% TFA buffer; 30 minutes; 1 mL/min) $t_r$=15.77 min.

Example 12

3-{6-[butyl(methyl)amino]-4-phenyl-2-pyridinyl}phenol

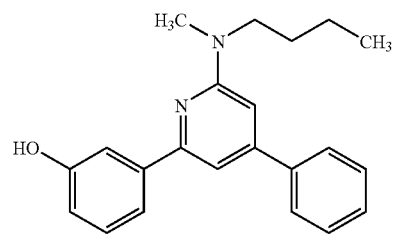

Example 12 was prepared from Intermediate 11, 1H-1,2,3-benzotriazol-1-ylacetonitrile, and N-methyl-N-propylamine by an identical procedure as described in Example 1 to afford 7 mg of a tan oil. Low resolution MS (ES⁺) m/e 333 (MH⁺); RP-HPLC (Dynamax C-18 25 cm×4.1 mm; 10-100% CH₃CN in H₂O with 0.1% TFA buffer; 30 minutes; 1 mL/min) $t_r$=17.22 min.

Example 13

4-{6-[butyl(methyl)amino]-4-phenyl-2-pyridinyl}-3-methylphenol

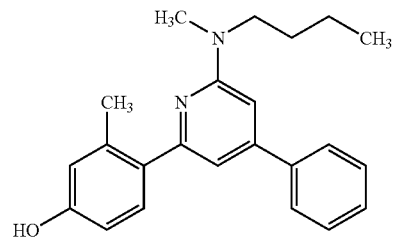

Example 13 was prepared from Intermediate 12, 1H-1,2,3-benzotriazol-1-ylacetonitrile, and N-methyl-N-propylamine by an identical procedure as described in Example 1 to afford 5 mg of a brown oil. Low resolution MS (ES+) m/e 347 (MH+); RP-HPLC (Dynamax C-18 25 cm×4.1 mm; 10-100% CH₃CN in H₂O with 0.1% TFA buffer; 30 minutes; 1 mL/min) t$_r$=17.89 min.

Example 14

4-[6-[butyl(methyl)amino]-4-(2-methylphenyl)-2-pyridinyl]phenol

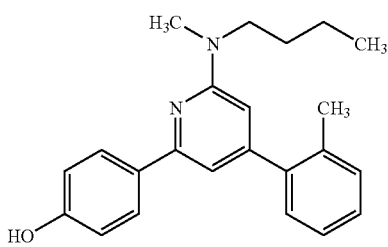

Example 14 was prepared from Intermediate 13, 1H-1,2,3-benzotriazol-1-ylacetonitrile, and N-methyl-N-propylamine by an identical procedure as described in Example 1 to afford 5 mg of a brown oil. Low resolution MS (ES+) m/e 347 (MH+); RP-HPLC (Dynamax C-18 25 cm×4.1 mm; 10-100% CH₃CN in H₂O with 0.1% TFA buffer; 30 minutes; 1 mL/min) t$_r$=17.66 min.

Example 15

4-{6-[benzyl(methyl)amino]-4-phenyl-2-pyridinyl}-3-methylphenol

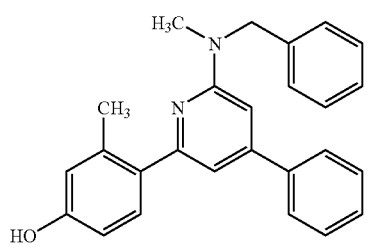

Example 15 was prepared from Intermediate 12, 1H-1,2,3-benzotriazol-1-ylacetonitrile, and N-methyl-N-benzylamine by an identical procedure as described in Example 1 to afford 14 mg of a clear oil. Low resolution MS (ES+) m/e 381 (MH+); RP-HPLC (Dynamax C-18 25 cm×4.1 mm; 10-100% CH₃CN in H₂O with 0.1% TFA buffer; 30 minutes; 1 mL/min) t$_r$=19.03 min.

Example 16

4-{6-[benzyl(methyl)amino]-4-phenyl-2-pyridinyl}phenol

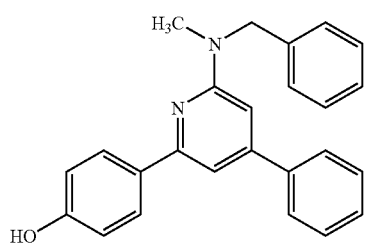

Example 16 was prepared from Intermediate 9, 1H-1,2,3-benzotriazol-1-ylacetonitrile, and N-methyl-N-benzylamine by an identical procedure as described in Example 1 to afford 9 mg of a yellow oil. Low resolution MS (ES+) m/e 367 (MH+); RP-HPLC (Dynamax C-18 25 cm×4.1 mm; 10-100% CH₃CN in H₂O with 0.1% TFA buffer; 30 minutes; 1 mL/min) t$_r$=18.52 min.

Example 17

4-{6-[methyl(1-naphthylmethyl)amino]-4-phenyl-2-pyridinyl}phenol

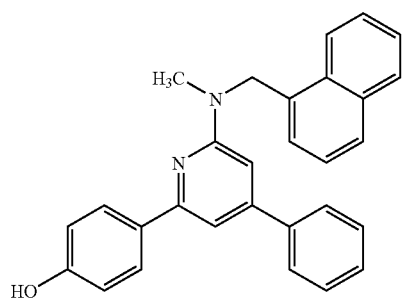

Example 17 was prepared from Intermediate 9, 1H-1,2,3-benzotriazol-1-ylacetonitrile, and N-methyl-N-(1-naphthyl)amine by an identical procedure as described in Example 1 to afford 8 mg of a yellow oil. Low resolution MS (ES+) m/e 417 (MH+); RP-HPLC (Dynamax C-18 25 cm×4.1 mm; 10-100% CH₃CN in H₂O with 0.1% TFA buffer; 30 minutes; 1 mL/min) t$_r$=20.45 min.

Example 18

3-methyl-4-{6-[methyl(1-naphthylmethyl)amino]-4-phenyl-2-pyridinyl}phenol

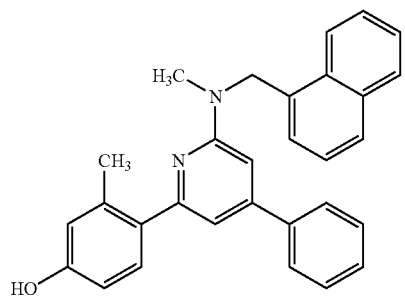

Example 18 was prepared from Intermediate 12, 1H-1,2,3-benzotriazol-1-ylacetonitrile, and N-methyl-N-(1-naphthyl)amine by an identical procedure as described in Example 1 to afford 7 mg of a yellow oil. Low resolution MS (ES+) m/e 431 (MH+); RP-HPLC (Dynamax C-18 25 cm×4.1 mm; 10-100% CH₃CN in H₂O with 0.1% TFA buffer; 30 minutes; 1 mL/min) t$_r$=20.66 min.

Example 19

2-methyl-4-{6-[methyl(1-naphthylmethyl)amino]-4-phenyl-2-pyridinyl}phenol

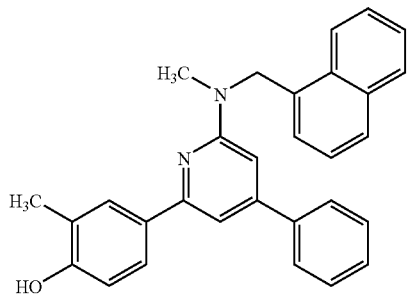

Example 19 was prepared from Intermediate 14, 1H-1,2,3-benzotriazol-1-ylacetonitrile, and N-methyl-N-(1-naphthyl)amine by an identical procedure as described in Example 1 to afford 9 mg of a yellow oil. Low resolution MS (ES$^+$) m/e 431 (MH$^+$); RP-HPLC (Dynamax C-18 25 cm×4.1 mm; 10-100% CH$_3$CN in H$_2$O with 0.1% TFA buffer; 30 minutes; 1 mL/min) t$_r$=20.29 min.

Example 20

4-{6-[isopentyl(methyl)amino]-4-phenyl-2-pyridinyl}phenol

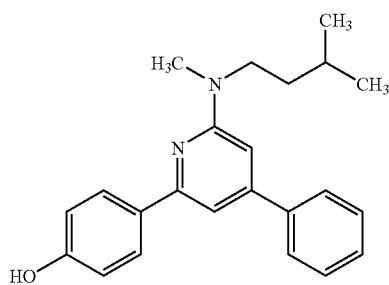

Example 20 was prepared from Intermediate 9, 1H-1,2,3-benzotriazol-1-ylacetonitrile, and N-methyl-N-isopentylamine by an identical procedure as described in Example 1 to afford 10 mg of a yellow oil. Low resolution MS (ES$^+$) m/e 347 (MH$^+$); RP-HPLC (Dynamax C-18 25 cm×4.1 mm; 10-100% CH$_3$CN in H$_2$O with 0.1% TFA buffer; 30 minutes; 1 mL/min) t$_r$=17.66 min.

Example 21

4-{6-[isopentyl(methyl)amino]-4-phenyl-2-pyridinyl}-3-methylphenol

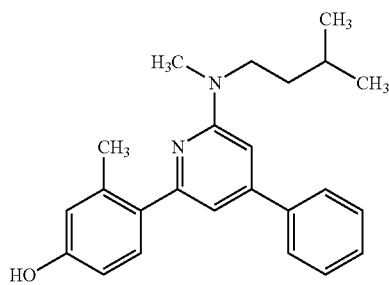

Example 21 was prepared from Intermediate 12, 1H-1,2,3-benzotriazol-1-ylacetonitrile, and N-methyl-N-isopentylamine by an identical procedure as described in Example 1 to afford 10 mg of a yellow oil. Low resolution MS (ES$^+$) m/e 361 (MH$^+$); RP-HPLC (Dynamax C-18 25 cm×4.1 mm; 10-100% CH$_3$CN in H$_2$O with 0.1% TFA buffer; 30 minutes; 1 mL/min) t$_r$=17.92 min.

Example 22

4-(6-{methyl[2-(2-pyridinyl)ethyl]amino}-4-phenyl-2-pyridinyl)phenol

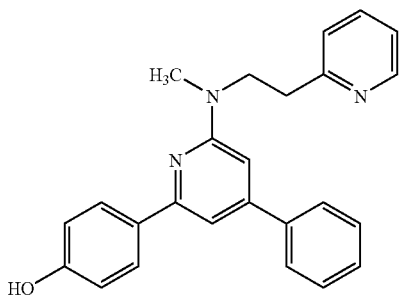

Example 22 was prepared from Intermediate 9, 1H-1,2,3-benzotriazol-1-ylacetonitrile, and N-methyl-2-(2-pyridinyl)ethylamine by an identical procedure as described in Example 1 to afford 7 mg of a yellow oil. Low resolution MS (ES$^+$) m/e 382 (MH$^+$); RP-HPLC (Dynamax C-18 25 cm×4.1 mm; 10-100% CH$_3$CN in H$_2$O with 0.1% TFA buffer; 30 minutes; 1 mL/min) t$_r$=13.78 min.

Example 23

3-methyl-4-(6-{methyl[2-(2-pyridinyl)ethyl]amino}-4-phenyl-2-pyridinyl)phenol

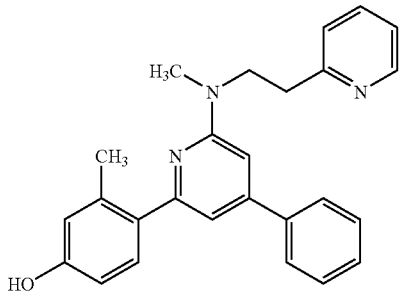

Example 23 was prepared from Intermediate 12, 1H-1,2,3-benzotriazol-1-ylacetonitrile, and N-methyl-2-(2-pyridinyl)ethylamine by an identical procedure as described in Example 1 to afford 7 mg of a yellow oil. Low resolution MS (ES$^+$) m/e 396 (MH$^+$); RP-HPLC (Dynamax C-18 25 cm×4.1 mm; 10-100% CH$_3$CN in H$_2$O with 0.1% TFA buffer; 30 minutes; 1 mL/min) t$_r$=14.02 min.

Example 24

2-methyl-4-(6-{methyl[2-(2-pyridinyl)ethyl]amino}-4-phenyl-2-pyridinyl)phenol

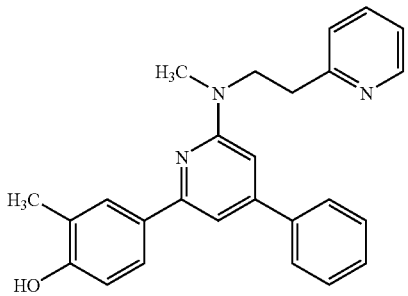

Example 24 was prepared from Intermediate 14, 1H-1,2,3-benzotriazol-1-ylacetonitrile, and N-methyl-2-(2-pyridinyl)ethylamine by an identical procedure as described in Example 1 to afford 5 mg of a yellow oil. Low resolution MS (ES$^+$) m/e 396 (MH$^+$); RP-HPLC (Dynamax C-18 25 cm×4.1 mm; 10-100% CH$_3$CN in H$_2$O with 0.1% TFA buffer; 30 minutes; 1 mL/min) t$_r$=14.52 min.

Example 25

4-{4-phenyl-6-[propyl(2-pyridinylmethyl)amino]-2-pyridinyl}phenol

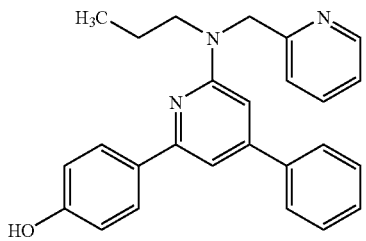

Example 25 was prepared from Intermediate 9, 1H-1,2,3-benzotriazol-1-ylacetonitrile, and N-2-(pyridinylmethyl)-1-propylamine by an identical procedure as described in Example 1 to afford 5 mg of a yellow oil. Low resolution MS (ES$^+$) m/e 396 (MH$^+$); RP-HPLC (Dynamax C-18 25 cm×4.1 mm; 10-100% CH$_3$CN in H$_2$O with 0.1% TFA buffer; 30 minutes; 1 mL/min) t$_r$=13.93 min.

Example 26

3-methyl-4-{4-phenyl-6-[propyl(2-pyridinylmethyl)amino]-2-pyridinyl}phenol

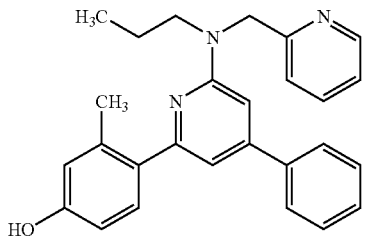

Example 26 was prepared from Intermediate 12, 1H-1,2,3-benzotriazol-1-ylacetonitrile, and N-2-(pyridinylmethyl)-1-propylamine by an identical procedure as described in Example 1 to afford 5 mg of a yellow oil. Low resolution MS (ES$^+$) m/e 410 (MH$^+$); RP-HPLC (Dynamax C-18 25 cm×4.1 mm; 10-100% CH$_3$CN in H$_2$O with 0.1% TFA buffer; 30 minutes; 1 mL/min) t$_r$=14.25 min.

Example 27

4-(6-{benzyl[2-(dimethylamino)ethyl]amino}-4-phenyl-2-pyridinyl)-3-methylphenol

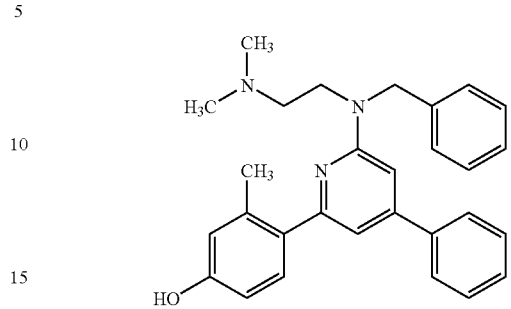

Example 27 was prepared from Intermediate 12, 1H-1,2,3-benzotriazol-1-ylacetonitrile, and N$^1$-benzyl-N$^2$,N$^2$-dimethylethylenediamine by an identical procedure as described in Example 1 to afford 5 mg of a yellow oil. Low resolution MS (ES$^+$) m/e 424 (MH$^+$); RP-HPLC (Dynamax C-18 25 cm×4.1 mm; 10-100% CH$_3$CN in H$_2$O with 0.1% TFA buffer; 30 minutes; 1 mL/min) t$_r$=11.58 min.

Example 28

4-{6-[ethyl(4-pyridinylmethyl)amino]-4-phenyl-2-pyridinyl}-3-methylphenol

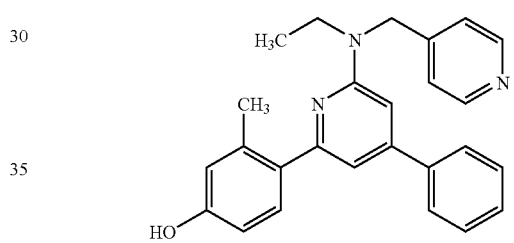

Example 28 was prepared from Intermediate 12, 1H-1,2,3-benzotriazol-1-ylacetonitrile, and N-4-pyridinylmethyl-N-ethylamine by an identical procedure as described in Example 1 to afford 6 mg of a brown oil. Low resolution MS (ES$^+$) m/e 396 (MH$^+$); RP-HPLC (Dynamax C-18 25 cm×4.1 mm; 10-100% CH$_3$CN in H$_2$O with 0.1% TFA buffer; 30 minutes; 1 mL/min) t$_r$=14.77 min.

Example 29

4-[6-(4-benzyl-1-piperidinyl)-4-phenyl-2-pyridinyl]-3-methylphenol

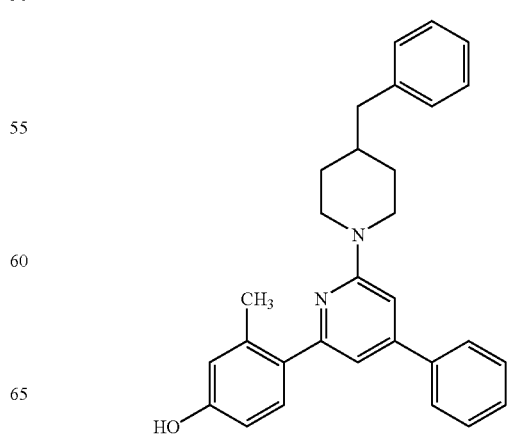

Example 29 was prepared from Intermediate 12, 1H-1,2,3-benzotriazol-1-ylacetonitrile, and 4-benzylpiperidine by an identical procedure as described in Example 1 to afford 8 mg of a yellow oil. Low resolution MS (ES$^+$) m/e 435 (MH$^+$); RP-HPLC (Dynamax C-18 25 cm×4.1 mm; 10-100% CH$_3$CN in H$_2$O with 0.1% TFA buffer; 30 minutes; 1 mL/min) t$_r$=17.57 min.

Example 30

4-[6-(4-benzyl-1-piperidinyl)-4-phenyl-2-pyridinyl]phenol

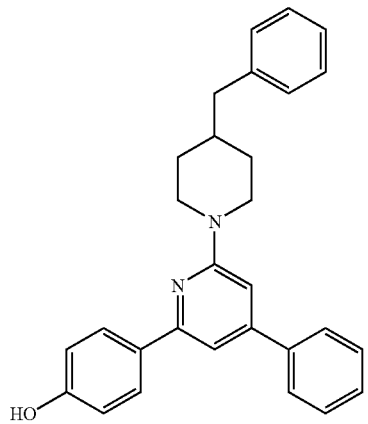

Example 30 was prepared from Intermediate 9, 1H-1,2,3-benzotriazol-1-ylacetonitrile, and 4-benzylpiperidine by an identical procedure as described in Example 1 to afford 4 mg of a yellow oil. Low resolution MS (ES$^+$) m/e 421 (MH$^+$); RP-HPLC (Dynamax C-18 25 cm×4.1 mm; 10-100% CH$_3$CN in H$_2$O with 0.1% TFA buffer; 30 minutes; 1 mL/min) t$_r$=17.33 min.

Example 31

4-{6-[benzyl(2-phenylethyl)amino]-4-phenyl-2-pyridinyl}-3-methylphenol

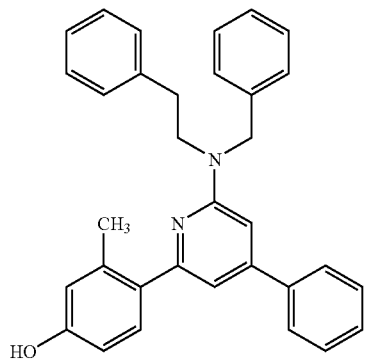

Example 31 was prepared from Intermediate 12, 1H-1,2,3-benzotriazol-1-ylacetonitrile, and N-benzyl-N-2-phenethylamine by an identical procedure as described in Example 1 to afford 4 mg of a yellow oil. Low resolution MS (ES$^+$) m/e 472 (MH$^+$); RP-HPLC (Dynamax C-18 25 cm×4.1 mm; 10-100% CH$_3$CN in H$_2$O with 0.1% TFA buffer; 30 minutes; 1 mL/min) t$_r$=20.69 min.

Example 32

4-{6-[bis(2-ethoxyethyl)amino]-4-phenyl-2-pyridinyl}-3-methylphenol

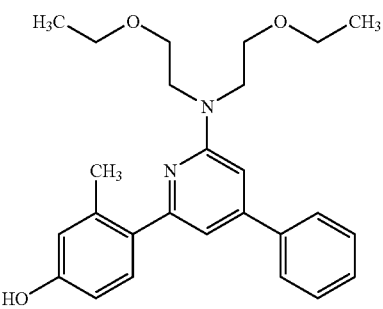

Example 32 was prepared from Intermediate 12, 1H-1,2,3-benzotriazol-1-ylacetonitrile, and N,N-bis-2-ethoxyethylamine by an identical procedure as described in Example 1 to afford 5 mg of a clear oil. Low resolution MS (ES$^+$) m/e 421 (MH$^+$); RP-HPLC (Dynamax C-18 25 cm×4.1 mm; 10-100% CH$_3$CN in H$_2$O with 0.1% TFA buffer; 30 minutes; 1 mL/min) t$_r$=15.90 min.

BIOLOGICAL DATA

Protein Preparation:

The ligand binding domain of both ERα and ERβ were subcloned into pGEX-2T vector, which had been modified to contain KpnI and BamHI restriction, sites in the multiple cloning region. GST-hERα and GST-hERβ proteins were made by transforming BL21(DE3)pLYS S competent cells with the appropriate expression plasmid. Liquid cultures containing standard Luria-Bertani (LB) broth with 0.1 mg/ml ampicillin and 0.033 mg/ml chloramphenicol were grown at 37° C. to an OD600 of 0.5-1.0 then induced with IPTG for 2-3 hours. The cells were collected by centrifugation and resuspended in lysis buffer (50 mM Tris pH 7.9; 250 mM KCl; 1% Triton X-100; 10 mM DTT; 1 mM PMSF). The lysate was then placed on dry ice until completely frozen. The frozen lysate was thawed and centrifuged 20 min at 4° C. at 80 K rpm in a TLA 100.2 rotor in a Beckman TL-100 ultracentrifuge. The supernatant was retained and glycerol was added to a final concentration of 10%. The protein content of the supernatant was quantitated using the BioRad Protein Assay Reagent. The protein was then stored at −80° C. until used in the binding assay.

Competition Binding Assay:

Polylysine coated Yttrium Silicate SPA beads (Amersham #RPNQ 0010) was resuspended in assay buffer [10 mM potassium phosphate buffer pH 7.0 containing 2 mM EDTA, 50 mM NaCl, 1 mM DTT, 2 mM CHAPS, 10% glycerol] to a concentration of 1 g/60 ml. 30 ul (0.5 mg) of the SPA beads was then added to each well of a Packard OptiPlate (Packard 6005190, Packard Instruments, Meriden, Conn.). The ERα or ERβ protein was diluted to the appropriate concentration (empirically determined for each protein prep by generating a protein curve using 0.5 to 10 ug total protein and 1 nM [3H]Estradiol and selecting a protein concentration that does not deplete the radioligand) and added as 30 ul aliquots to each well. [2, 4, 6, 7, 16, 17-3H(N)]-Estradiol was added as a 30 ul aliquot to give a final assay concentration of 1 nM. To give a final volume of 100 ul, either 10 ul of a test compound solution (typically in 10% DMSO as solvent), solvent containing no test compound (to determine total binding, T), or solvent containing 17-b-estradiol at 100 uM (to determine non-specific binding, NS) were finally added to the plate. The plates were shaken vigorously for two hours then counted on a Packard TopCount using the protocol for counting tritium yttrium silicate SPA beads. Data analysis was done by standard methods. % Bound was calculated for each concentration of each test compound using the equation % Bound=100*((Test−NS)/(T−NS)). % Bound was plotted vs concentration and curve fitting was accomplished using non-linear regression.

Saturation Binding Assay:

Saturation binding assays were run similarly to competition assays. Dissociation constants (Kd) were determined by generating twelve-point saturation curves using 10 uM 17-b-estradiol to define nonspecific binding. [2, 4, 6, 7, 16, 17-3H(N)]-Estradiol was added such that the final concentration ranged from 0.1 to 100 nM.

| | Estrogen Receptor Binding | |
|---|---|---|
| Example # | Avg. ER alpha $K_i$ (n) | Avg. ER beta $K_I$ (n) |
| 1 | 490 nM (4) | 1050 nM (4) |
| 2 | >3000 nM (2) | >3000 nM (2) |
| 6 | 160 nM (4) | 680 nM (4) |
| 7 | 650 nM (2) | 1100 nM (2) |
| 12 | 660 nM (2) | 790 nM (4) |
| 15 | 380 nM (4) | 1120 nM (2) |
| 18 | 450 nM (2) | 1410 nM (2) |
| 20 | 620 nM (2) | 1260 nM (4) |
| 21 | 210 nM (2) | 660 nM (2) |
| 23 | 1260 nM (2) | >3000 nM (2) |
| 25 | 180 nM (4) | 710 nM (6) |
| 26 | 70 nM (4) | 330 nM (6) |
| 28 | 830 nM (4) | 1000 nM (6) |
| 29 | 20 nM (4) | 110 nM (4) |
| 31 | 130 nM (2) | 250 nM (2) |
| 32 | 2000 nM (2) | 1170 nM (2) |

We claim:

1. A compound of Formula (I):

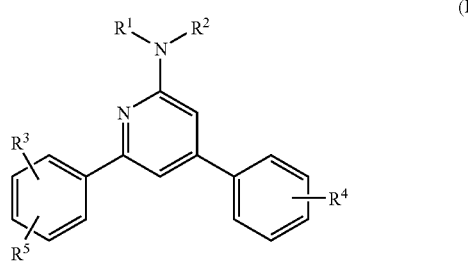

(I)

or a salt, or solvate thereof:
wherein:
$R^1$ is $C_1$-$C_6$ alkyl or —$(CH_2)_mR^6$ and $R^2$ is n-butyl, isopentyl, or —$(CH_2)_mR^6$; or
$R^1$ is —$CH_2CH_2$-(ethylene) and $R^2$ is —$CH_2CH_2CH_2$-(propylene) and $R^1$ and $R^2$ are linked together with the nitrogen to which they are attached to form a piperidine group substituted with aralkyl;
$R^3$, $R^4$, and $R^5$ are independently selected from hydrogen, hydroxy, ($C_1$-$C_6$)alkyl, halo, or —OR';
m is 0, 1, 2, 3, 4, 5, or 6;
$R^6$ is aryl, heteroaryl, —NR'R", or —OR'; and R' and R" are independently selected from hydrogen, or $C_1$-$C_6$ alkyl.

2. A compound as claimed in claim 1, wherein $R^1$ is methyl, ethyl, or propyl.

3. A compound as claimed in claim 1, wherein $R^1$ is —$(CH_2)_mR^6$ where m is 2 and $R^6$ is phenyl, —$OCH_2CH_3$, or —$N(CH_3)_2$.

4. A compound as claimed in claim 1, wherein $R^2$ is n-butyl or isopentyl.

5. A compound as claimed in claim 1, wherein $R^2$ is —$(CH_2)_mR^6$ where m is 1 or 2 and $R^6$ is phenyl, pyridyl, napthyl, or —$OCH_2CH_3$.

6. A compound as claimed in claim 1, wherein the aralkyl is benzyl.

7. A compound as claimed in claim 1, wherein $R^3$ is hydrogen, $C_1$-$C_6$ alkyl or hydroxy.

8. A compound as claimed in claim 1, wherein $R^3$ is hydrogen, methyl, or hydroxy.

9. A compound as claimed in claim 1, wherein $R^3$ is hydroxy.

10. A compound as claimed in claim 1, wherein $R^4$ is hydrogen or $C_1$-$C_6$ alkyl.

11. A compound as claimed in claim 1, wherein $R^4$ hydrogen or methyl.

12. A compound as claimed in claim 1, wherein $R^4$ hydrogen.

13. A compound as claimed in claim 1, wherein $R^5$ is hydrogen, $C_1$-$C_6$ alkyl or hydroxy.

14. A compound as claimed in claim 1, wherein $R^5$ is hydrogen, methyl, or hydroxy.

15. A compound as claimed in claim 1, wherein $R^5$ is hydrogen.

16. A compound as claimed in claim 1, wherein $R^1$ is $C_1$-$C_6$ alkyl or —$(CH_2)_mR^6$; $R^2$ is n-butyl, isopentyl, or —$(CH_2)_mR^6$; $R^3$ is hydrogen, $C_1$-$C_6$ alkyl or hydroxy; $R^4$ is hydrogen or $C_1$-$C_6$ alkyl; and $R^5$ hydrogen, $C_1$-$C_6$ alkyl or hydroxy.

17. A compound as claimed in claim 1, wherein $R^1$ is —$CH_2CH_2$-(ethylene) and $R^2$ is —$CH_2CH_2CH_2$-(propylene) and $R^1$ and $R^2$ are linked together with the nitrogen to which they are attached to form a piperidine group substituted with aralkyl; $R^3$ is hydrogen, $C_1$-$C_6$ alkyl or hydroxy; $R^4$ is hydrogen or $C_1$-$C_6$ alkyl; and $R^5$ is hydrogen, $C_1$-$C_6$ alkyl or hydroxy.

18. A compound as claimed in claim 17, wherein the aralkyl is benzyl.

19. A compound as claimed in claim 1, wherein $R^1$ is methyl, ethyl, or propyl; $R^2$ is n-butyl or isopentyl; $R^3$ is hydrogen, $C_1$-$C_6$ alkyl, or hydroxy; $R^4$ is hydrogen or $C_1$-$C_6$ alkyl; and $R^5$ is hydrogen, $C_1$-$C_6$ alkyl or hydroxy.

20. A compound as claimed in claim 1, wherein $R^1$ is methyl, ethyl, or propyl; $R^2$ is —$(CH_2)_mR^6$ where m is 1 or 2 and $R^6$ is phenyl, pyridyl, napthyl, or —$OCH_2CH_3$; $R^3$ is hydrogen, $C_1$-$C_6$ alkyl, or hydroxy; $R^4$ is hydrogen or $C_1$-$C_6$ alkyl; and $R^5$ is hydrogen, $C_1$-$C_6$ alkyl or hydroxy.

21. A compound as claimed in claim 1, wherein $R^1$ is —$(CH_2)_mR^6$ where m is 2 and $R^6$ is phenyl, —$OCH_2CH_3$, or —$N(CH_3)_2$; $R^2$ is —$(CH_2)_mR^6$ where m is 1 or 2 and $R^5$ is phenyl, pyridyl, napthyl, or —$OCH_2CH_3$; $R^3$ is hydrogen, $C_1$-$C_6$ alkyl, or hydroxy; $R^4$ is hydrogen or $C_1$-$C_6$ alkyl; and $R^5$ hydrogen, $C_1$-$C_6$ alkyl or hydroxy.

22. A compound as claimed in claim 1, wherein $R^1$ is $C_1$-$C_6$ alkyl or —$(CH_2)_mR^6$; $R^2$ is n-butyl, isopentyl, or —$(CH_2)_mR^6$; $R^3$ is hydroxy; $R^4$ is hydrogen or methyl; and $R^5$ is hydrogen, methyl or hydroxy.

23. A compound as claimed in claim 1, wherein $R^1$ is $C_1$-$C_6$ alkyl or —$(CH_2)_mR^6$; $R^2$ is n-butyl, isopentyl, or —$(CH_2)_mR^6$; $R^4$ is hydroxy; $R^4$ is hydrogen; and $R^5$ hydrogen.

24. A compound as claimed in claim 1, wherein $R^1$ is methyl, ethyl, or propyl; $R^2$ is —$CH_2)_mR^6$ where m is 1 or 2 and $R^6$ is phenyl, pyridyl, napthyl, or —$OCH_2CH_3$;
$R^3$ is hydroxy; $R^4$ is hydrogen or methyl; and $R^5$ is hydrogen, methyl or hydroxy.

25. A compound as claimed in claim 1, wherein $R^1$ is —$(CH_2)_mR^6$ where m is 2 and $R^6$ is phenyl, —$OCH_2CH_3$, or —$N(CH_3)_2$; $R^2$ is —$(CH_2)_mR^6$ where m is 1 or 2 and $R^6$ is phenyl, pyridyl, napthyl, or —$OCH_2CH_3$; $R^3$ is hydroxy; $R^4$ is hydrogen or methyl; and $R^5$ is hydrogen, methyl or hydroxy.

26. A compound selected from the group:
4-{6-[methyl(2-phenylethyl)amino]-4-phenyl-2-pyridinyl}phenol;
4-{6-[methyl(2-phenylethyl)amino]-(4-hydroxy)phenyl-2-pyridinyl}phenol;
3-{6-[methyl(2-phenylethyl)amino]-(4-hydroxy)phenyl-2-pyridinyl}phenol;
3-{6-[methyl(2-phenylethyl)amino]-(3-hydroxy)phenyl-2-pyridinyl}phenol;
3-{6-[methyl(2-phenylethyl)amino]-4-phenyl-2-pyridinyl}phenol;
3-methyl-4-{6-[methyl(2-phenylethyl)amino]-4-phenyl-2-pyridinyl}phenol;
4-{4-(2-methylphenyl)-6-[methyl(2-phenylethyl)amino]-2-pyridinyl}phenol;
4-{6-(butyl(methyl)amino]-4-phenyl-2-pyridinyl}phenol;
4-{6-[butyl(methyl)amino]-(4-hydroxy)phenyl-2-pyridinyl}phenol;
3-{6-[butyl(methyl)amino]-(4-hydroxy)phenyl-2-pyridinyl}phenol;
3-{6-[butyl(methyl)amino]-(3-hydroxy)phenyl-2-pyridinyl}phenol;
3-{6-[butyl(methyl)amino]-4-phenyl-2-pyridinyl}phenol;
4-{6-[butyl(methyl)amino]-4-phenyl-2-pyridinyl}-3-methylphenol;
4-[6-[butyl(methyl)amino]-4-(2-methylphenyl)-2-pyridinyl]phenol;
4-{6-[benzyl(methyl)amino]-4-phenyl-2-pyridinyl}-3-methylphenol;
4-{6-[benzyl(methyl)amino]-4-phenyl-2-pyridinyl}phenol;
4-{6-[methyl(1-naphthylmethyl)amino]-4-phenyl-2-pyridinyl}phenol;
3-methyl-4-{6-[methyl(1-naphthylmethyl)amino]-4-phenyl-2-pyridinyl}phenol;
2-methyl-4-{6-[methyl(1-naphthylmethyl)amino]-4-phenyl-2-pyridinyl}phenol;
4-{6-[isopentyl(methyl)amino]-4-phenyl-2-pyridinyl}phenol;
4-{6-[isopentyl(methyl)amino]-4-phenyl-2-pyridinyl}-3-methylphenol;
4-(6-{methyl[2-(2-pyridinyl)ethyl]amino}-4-phenyl-2-pyridinyl)phenol;
3-methyl-4-(6-{methyl[2-(2-pyridinyl)ethyl]amino}-4-phenyl-2-pyridinyl)phenol;
2-methyl-4-(6-{methyl[2-(2-pyridinyl)ethyl]amino}-4-phenyl-2-pyridinyl)phenol;
4-{4-phenyl-6-[propyl(2-pyridinyl methyl)amino]-2-pyridinyl}phenol;
3-methyl-4-{4-phenyl-6-[propyl(2-pyridinylmethyl)amino]-2-pyridinyl}phenol;
4-(6-{benzyl[2-(dimethylamino)ethyl]amino}-4-phenyl-2-pyridinyl)-3-methylphenol;
4-{6-[ethyl(4-pyridinylmethyl)amino]-4-phenyl-2-pyridinyl}-3-methylphenol;
4-[6-(4-benzyl-1-piperidinyl)-4-phenyl-2-pyridinyl]-3-methylphenol;
4-[6-(4-benzyl-1-piperidinyl)-4-phenyl-2-pyridinylphenol;
4-{6-[benzyl(2-phenylethyl)amino]-4-phenyl-2-pyridinyl}-3-methylphenol; and
4-{6-[bis(2-ethoxyethyl)amino]-4-phenyl-2-pyridinyl}-3-methylphenol;
or a salt, or solvate thereof.

27. A pharmaceutical composition, comprising: a therapeutically effective amount of a compound as claimed in claim 1, or a salt, or solvate, thereof and one or more of pharmaceutically acceptable carriers, diluents and excipients.

* * * * *